United States Patent
Ryu et al.

(10) Patent No.: US 12,051,586 B2
(45) Date of Patent: Jul. 30, 2024

(54) METHOD OF MANUFACTURING SEMICONDUCTOR DEVICE

(71) Applicant: SAMSUNG ELECTRONICS CO., LTD., Suwon-si (KR)

(72) Inventors: Seung-Min Ryu, Hwaseong-si (KR); Jiyu Choi, Suwon-si (KR); Gyu-Hee Park, Hwaseong-si (KR); Younjoung Cho, Hwaseong-si (KR)

(73) Assignee: SAMSUNG ELECTRONICS CO., LTD., Gyeonggi-do (KR)

( * ) Notice: Subject to any disclaimer, the term of this patent is extended or adjusted under 35 U.S.C. 154(b) by 988 days.

(21) Appl. No.: 17/022,198

(22) Filed: Sep. 16, 2020

(65) Prior Publication Data

US 2021/0175073 A1   Jun. 10, 2021

(30) Foreign Application Priority Data

Dec. 9, 2019 (KR) .......................... 10-2019-0162925
Mar. 25, 2020 (KR) .......................... 10-2020-0036213
Sep. 10, 2020 (KR) .......................... 10-2020-0115974

(51) Int. Cl.
*H01L 21/02* (2006.01)
*C01G 19/00* (2006.01)
(Continued)

(52) U.S. Cl.
CPC ........ *H01L 21/02205* (2013.01); *C01G 19/00* (2013.01); *C07C 211/08* (2013.01);
(Continued)

(58) Field of Classification Search
CPC . H01L 21/02205; C01G 19/00; C07C 211/08; C23C 16/08; C23C 16/18; C23C 16/303; C23C 16/45553
(Continued)

(56) References Cited

U.S. PATENT DOCUMENTS 4,957,775 A   9/1990 Black et al.
6,110,529 A   8/2000 Gardiner et al.
(Continued)

*Primary Examiner* — Monica D Harrison
(74) *Attorney, Agent, or Firm* — Muir Patent Law, PLLC

(57) ABSTRACT

A method of manufacturing a semiconductor device includes providing a metal precursor on a substrate, and providing a reactant and a co-reactant to form a metal nitride layer by reaction with the metal precursor, the reactant being a nitrogen source, the co-reactant being an organometallic compound represented by Chemical Formula 1:

$$M2{-}(L_1)_n \qquad \text{[Chemical Formula 1]}$$

In Chemical Formula 1, M2 may be selected from Sn, In, and Ge, n may be 2, 3, or 4, and each $L_1$ may independently be hydrogen, a halogen, or a group represented by Chemical Formula 2.

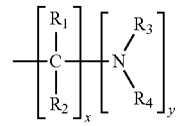

[Chemical Formula 2]

In Chemical Formula 2, x may be 0, 1, 2, 3, 4, or 5 and y may be 0 or 1. When x is 0, y may be 1. $R_1$, $R_2$, $R_3$, and $R_4$ may each independently be hydrogen, an alkyl group having 1 to 5 carbons, or an aminoalkyl group having 1 to 5 carbons.

20 Claims, 22 Drawing Sheets

(51) Int. Cl.
    *C07C 211/08*     (2006.01)
    *C23C 16/08*     (2006.01)
    *C23C 16/18*     (2006.01)
    *C23C 16/30*     (2006.01)
    *C23C 16/455*     (2006.01)

(52) U.S. Cl.
    CPC .............. *C23C 16/08* (2013.01); *C23C 16/18* (2013.01); *C23C 16/303* (2013.01); *C23C 16/45553* (2013.01)

(58) Field of Classification Search
    USPC ........................................................ 438/478
    See application file for complete search history.

(56) References Cited

U.S. PATENT DOCUMENTS

| | | |
|---|---|---|
| 6,355,545 B1 | 3/2002 | Ohba |
| 8,153,833 B2 * | 4/2012 | Wang ................. H01L 21/3144 |
| | | 556/412 |
| 9,831,094 B2 | 11/2017 | Rahtu et al. |
| 10,036,089 B2 | 7/2018 | Thompson et al. |
| 2007/0154637 A1 | 7/2007 | Shenai-Khatkhate et al. |
| 2020/0273747 A1 | 8/2020 | Ryu et al. |

* cited by examiner

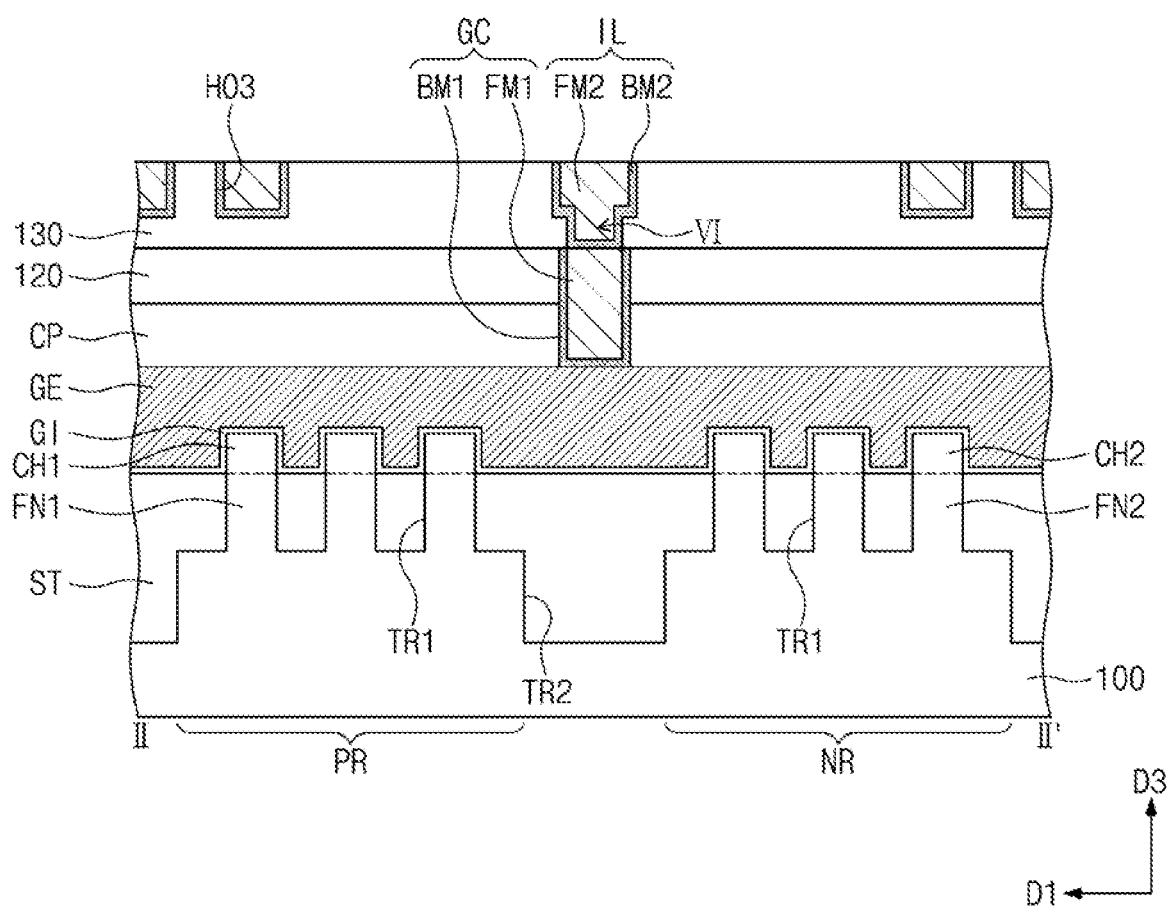

METHOD OF MANUFACTURING SEMICONDUCTOR DEVICE

CROSS-REFERENCE TO RELATED APPLICATION

Korean Patent Application Nos. 10-2019-0162925, filed on Dec. 9, 2019, 10-2020-0036213, filed on Mar. 25, 2020, and 10-2020-0115974, filed on Sep. 10, 2020, in the Korean Intellectual Property Office, and entitled: "Method of Manufacturing Semiconductor Device," are incorporated by reference herein in their entirety.

BACKGROUND

1. Field

Embodiments relate to a method of manufacturing a semiconductor device.

2. Description of the Related Art

Semiconductor devices are widely used in the electronic industry because of their small size, multi-functionality, and/or low manufacturing cost. Semiconductor devices may encompass a memory device for storing data, a logic device for processing data, and a hybrid device for operating various functions contemporaneously or simultaneously.

SUMMARY

Embodiments are directed to a method of manufacturing a semiconductor device, the method including providing a metal precursor on a substrate, and providing a reactant and a co-reactant to form a metal nitride layer by reaction with the metal precursor, the reactant being a nitrogen source, the co-reactant being an organometallic compound represented by Chemical Formula 1 below:

  [Chemical Formula 1]

In Chemical Formula 1, M2 may be selected from Sn, In, and Ge, n may be 2, 3, or 4, and each $L_1$ may independently be hydrogen, a halogen, or a functional group represented by Chemical Formula 2 below. At least one $L_1$ may be the functional group represented by Chemical Formula 2.

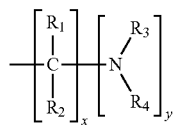  [Chemical Formula 2]

In Chemical Formula 2, x may be 0, 1, 2, 3, 4, or 5 and y may be 0 or 1. When x is 0, y may be 1. $R_1$, $R_2$, $R_3$, and $R_4$ may each independently be hydrogen, an alkyl group having 1 to 5 carbon atoms, or an aminoalkyl group having 1 to 5 carbon atoms.

Embodiments are also directed to a method of manufacturing a semiconductor device, the method including forming an active pattern on a substrate, forming a gate electrode extending across the active pattern, forming an active contact electrically connected to the active pattern and a gate contact electrically connected to the gate electrode, forming the active contact and the gate contact including forming a first hole exposing the active pattern and a second hole exposing the gate electrode, and forming a first metal nitride layer in the first hole and the second hole. Forming the first metal nitride layer may include providing a first metal precursor on the substrate to form a first preliminary layer, and providing, to the first preliminary layer, a first reactant that is a nitrogen source and a first co-reactant. The first co-reactant may be an organometallic compound represented by Chemical Formula 1 below:

  [Chemical Formula 1]

In Chemical Formula 1, M2 may be selected from Sn, In, and Ge, n may be 2, 3, or 4, and each $L_1$ may independently be hydrogen, a halogen, or a functional group represented by Chemical Formula 2 below. At least one $L_1$ may be the functional group represented by Chemical Formula 2.

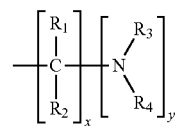  [Chemical Formula 2]

In Chemical Formula 2, x may be 0, 1, 2, 3, 4, or 5 and y may be 0 or 1. When x is 0, y may be 1. $R_1$, $R_2$, $R_3$, and $R_4$ may each independently be hydrogen, an alkyl group having 1 to 5 carbon atoms, or an aminoalkyl group having 1 to 5 carbon atoms.

Embodiments are also directed to a method of manufacturing a semiconductor device, the method including forming a first region including a plurality of transistors; and forming a second region stacked on the first region. Forming the second region may include forming a semiconductor layer on the first region, forming an active pattern on the semiconductor layer, and forming a capacitor electrically connected to the active pattern. Forming the capacitor may include forming a first electrode, forming a dielectric layer on the first electrode, and forming a second electrode on the dielectric layer. Forming at least one of the first and second electrodes may include providing a metal precursor to form a preliminary layer, and providing a reactant that is a nitrogen source and a co-reactant to the preliminary layer. The co-reactant may be an organometallic compound represented by Chemical Formula 1 below:

  [Chemical Formula 1]

In Chemical Formula 1, M2 may be selected from Sn, In, and Ge, n may be 2, 3, or 4, and each $L_1$ may independently be hydrogen, a halogen, or a functional group represented by Chemical Formula 2 below. At least one $L_1$ may be the functional group represented by Chemical Formula 2,

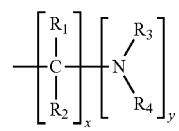  [Chemical Formula 2]

In Chemical Formula 2, x may be 0, 1, 2, 3, 4, or 5 and y may be 0 or 1. When x is 0, y may be 1. $R^1$, $R^2$, $R^3$, and $R^4$ may each independently be hydrogen, an alkyl group having 1 to 5 carbon atoms, or an aminoalkyl group having 1 to 5 carbon atoms.

BRIEF DESCRIPTION OF THE DRAWINGS

Features will become apparent to those of skill in the art by describing in detail example embodiments with reference to the attached drawings in which:

FIGS. 10B, 12B, 14B, and 16B illustrate cross-sectional views taken along line II-II' of FIGS. 9, 11, 13, and 15, respectively;

DETAILED DESCRIPTION

In the description, the phrase "substituted or unsubstituted" may indicate that one is substituted or unsubstituted with at least one substituent selected from the group of a hydrogen atom, a halogen atom, an alkyl group, a hydroxy group, an alkoxy group, an ether group, an alkenyl group, an aryl group, a hydrocarbon ring group, a heterocyclic group, and a combination thereof.

In the description, a halogen atom may include a fluorine atom, a chlorine atom, an iodine atom, and/or a bromine atom.

In the description, an alkyl group may be a linear alkyl group, a branched alkyl group, or a cyclic alkyl group. The number of carbons in the alkyl group may be 1 to 10, for example. Examples of the alkyl group may include, for example, a methyl group and an ethyl group.

Unless otherwise defined in Chemical Formulae of the description, the case where a chemical bond is not drawn in a position in which a chemical bond should be drawn may mean that a hydrogen atom is bonded to the position.

Figure 1:
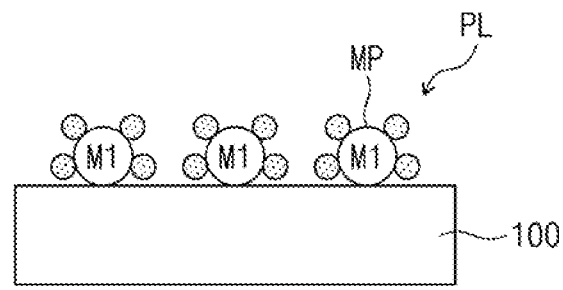
FIGS. 1 to 3 illustrate conceptual views of stages in a method of forming a metal-containing layer according to a comparative example.
Figure 2:
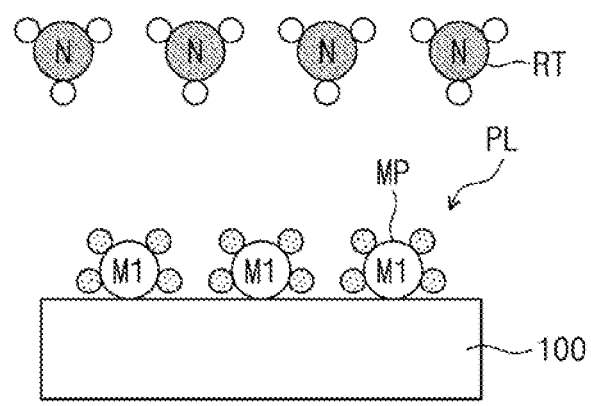
Figure 3:
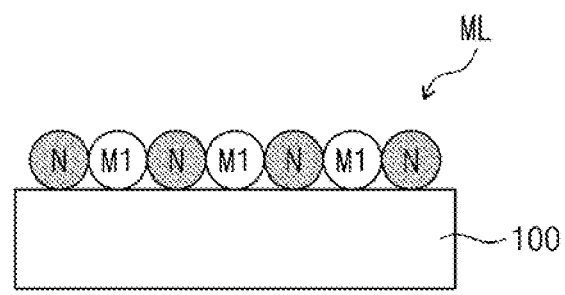
Figure 4:
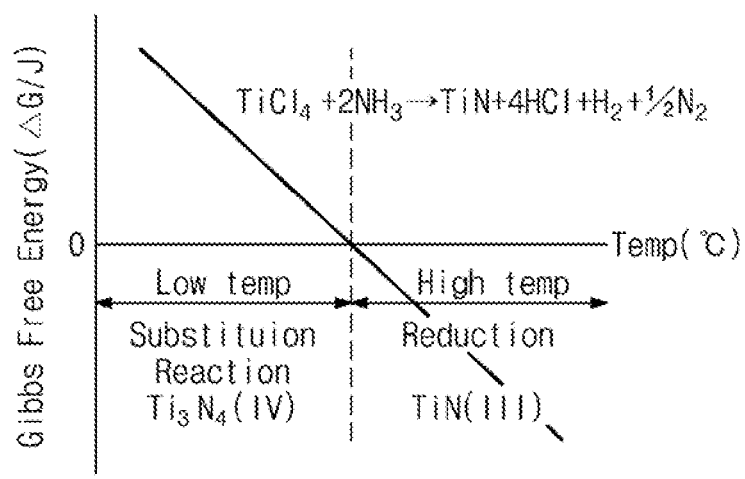
FIG. 4 is a graph showing Gibbs free energy depending on the temperature of a metal nitride reaction.

FIGS. 1 to 3 illustrate conceptual views of stages in a method of forming a metal-containing layer according to a comparative example. FIG. 4 is a graph showing Gibbs free energy depending on the temperature of a metal nitride reaction.

Referring to FIG. 1, a substrate 100 may be provided. A metal precursor MP may be provided on the substrate 100 to form a preliminary layer PL. An atomic layer deposition (ALD) or chemical vapor deposition (CVD) process may be used to form a metal-containing layer as the preliminary layer PL. The atomic layer deposition (ALD) or chemical vapor deposition (CVD) process may be performed at a process temperature of about 400° C. to about 800° C. and at a process pressure between 0 Torr and about 100 Torr.

The metal precursor MP may be, for example, a metal halide compound that contains a first metal M1 or an organometallic compound that contains the first metal M1. The first metal M1 may be selected from the group of Ti, Ta, Co, W, Ru, Mo, Sn, Cu, Ir, V, Al, and a combination thereof. For example, the metal halide compound may include $TiCl_4$, $WF_6$, $Ru(CO)_5$, $RuO_4$, $MoO_2C_2$, $MoCl_5$, $Mo_2Cl_{10}$, $CuCl_2$, $IrC_4$, $VC_3$, $VI_3$, $HfCl_4$, $NbCl_5$, or $TaCl_5$. For example, the metal organic compound may include PDMAT (pentakis(dimethylamino)tantalum) or TBTEMT (tert-butylimido-tris-ethylmethylamido-tantalum).

Referring to FIG. 2, a reactant RT may be provided on the preliminary layer PL. The reactant RT may be a nitrogen source compound that contains a nitrogen atom. For example, the reactant RT may include at least one selected from the group of $NH_3$, $N_2H_4$, $N_2$, and a combination thereof.

Referring to FIG. 3, the preliminary layer PL and the reactant RT may react with each other to form a metal-containing layer ML. The reactant RT may react with the preliminary layer PL to be substituted to the first metal M1 (i.e., substitution reaction). The reactant RT may react with the preliminary layer PL to reduce the first metal M1 (i.e., reduction reaction). Byproducts produced during the reaction may all be removed. The reactant RT may contain a nitrogen atom, and the metal-containing layer ML may be a metal nitride layer containing the first metal M1.

Referring to FIG. 4, when $TiCl_4$ is used as the metal precursor MP, and $NH_3$ is used as the reactant RT, $TiCl_4$ and $NH_3$ may be reacted to form a titanium nitride layer. The reduction reaction between $TiCl_4$ and $NH_3$ is as follows.

$$TiCl_4 + 2NH_3 \rightarrow TiN + 4HCl + H_2 + \tfrac{1}{2}N_2$$

In explaining the reduction reaction between $TiCl_4$ and $NH_3$, it may be understood that Gibbs free energy has a positive value in a low temperature realm (e.g., 400° C. or less). Thus, the reduction reaction between $TiCl_4$ and $NH_3$ is a nonspontaneous reaction at a low temperature of 400° C. or less.

Also, it may be understood that Gibbs free energy has a negative value in a high temperature realm (e.g., 400° C. or higher). Thus, the reduction reaction between $TiCl_4$ and $NH_3$ is a spontaneous reaction at a high temperature of 400° C. or higher.

The substitution reaction between $TiCl_4$ and $NH_3$ may dominate at a low temperature. Therefore, a metal nitride layer such as $Ti_3N_4(IV)$ may be formed at a low temperature, and Ti may have an oxidation number of +4. When the oxidation number of Ti of the titanium nitride layer is +4, free electrons are not present, and thus the resistivity may be significantly increased. Thus, the titanium nitride layer formed at a low temperature may be substantially an insulator.

The reduction reaction between $TiCl_4$ and $NH_3$ may dominate at a high temperature. Therefore, a metal nitride layer such as TiN(III) may be formed at a high temperature, and Ti may have an oxidation number of +3. When the oxidation number of Ti of the titanium nitride layer is +3, free electrons are present, and thus the resistivity may be decreased. Thus, the titanium nitride layer formed at a high temperature may be substantially a conductor.

As described above, in order to form a metal nitride layer having conductivity (i.e., a metal nitride layer having a relatively low resistivity), a high-temperature deposition process should be performed. Therefore, a deposition temperature according to the comparative example may be about 400° C. to about 600° C. However, in a semiconductor process for forming a semiconductor device, when a deposition process is performed at a high temperature, a lower layer that was formed in a preceding step may be deteriorated by being exposed to a high temperature environment. This may cause defective processes may degrade reliability of a semiconductor device.

In order to perform a deposition process for forming a metal nitride layer having conductivity at a relatively low temperature, plasma or a reactant having a strong reactivity (e.g., $N_2H_4$) may be used. However, plasma has poor step coverage characteristics, and thus may be difficult to be used in a region having a high aspect ratio. In addition, the reactant having a strong reactivity may be dangerous and difficult to handle.

Figure 5:
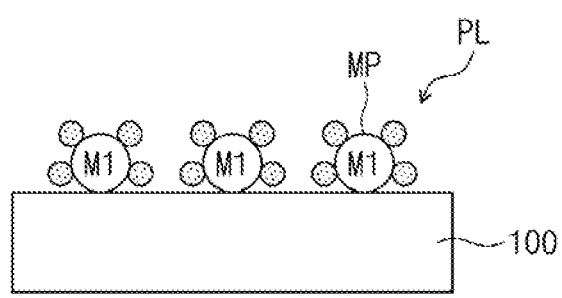
FIGS. 5 to 7 illustrate conceptual views of stages in a method of forming a metal-containing layer according to an example embodiment.
Figure 6:
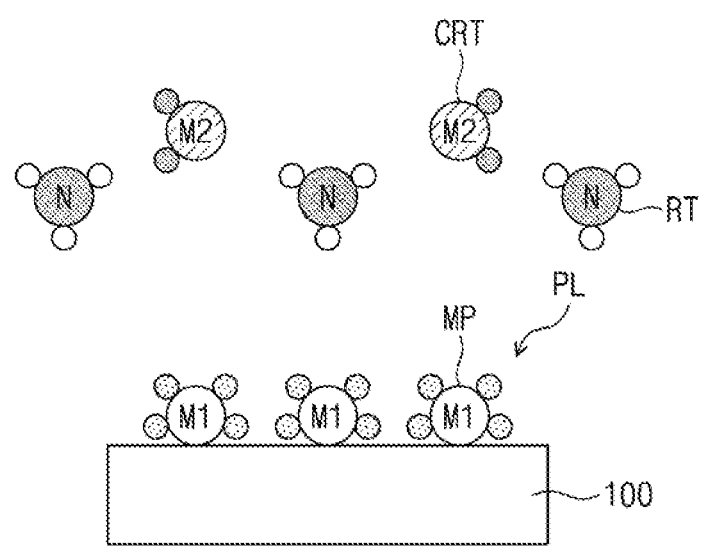
Figure 7:
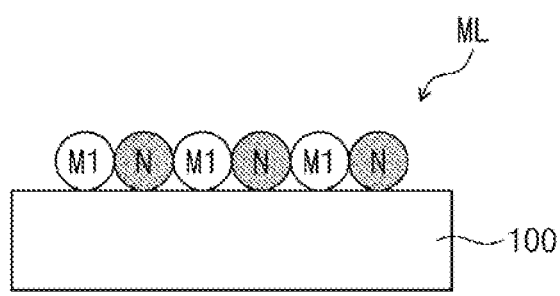

FIGS. 5 to 7 illustrate conceptual views of stages in a method of forming a metal-containing layer according to an example embodiment.

Referring to FIG. 5, a substrate 100 may be provided. A metal precursor MP may be provided on the substrate 100 to form a preliminary layer PL. The detailed description with respect to the metal precursor MP and the preliminary layer PL may be the same as those described above with reference to FIG. 1. An atomic layer deposition (ALD) or chemical vapor deposition (CVD) process may be used to form a metal-containing layer according to the present example. During a deposition process, a process pressure may be about 0 Torr to about 100 Torr, and a process temperature may be about 150° C. to about 600° C. For example, the deposition process according to the present example embodiment may be performed at a low temperature of about 150° C. to about 400° C. In an example embodiment, the preliminary layer may consist of or consist essentially of the metal precursor MP.

Referring to FIG. 6, a reactant RT and a co-reactant CRT may be provided on the preliminary layer PL. The detailed description with respect to the reactant RT may be the same as those described above with reference to FIG. 2. For example, the reactant RT may be $NH_3$.

The co-reactant CRT may serve as a catalyst that reduces an activation energy of the reduction reaction between the preliminary layer PL and the reactant RT. For example, the co-reactant CRT may reduce the first metal M1 of the preliminary layer PL. In an implementation, the co-reactant CRT may increase reducing power of the reactant RT. Accordingly, the co-reactant CRT may help spontaneously perform the reduction reaction between the preliminary layer PL and the reactant RT even at a low temperature (e.g., about 150° C. to about 400° C.).

For example, the co-reactant CRT may increase reducing power of ammonia, which has a low reducing power. Accordingly, the reduction reaction in which ammonia reduces the preliminary layer PL may be performed at a low temperature, and thereby a metal nitride layer having conductivity may be formed.

In an example embodiment, the co-reactant CRT may be provided on the preliminary layer PL, and thereafter the reactant RT may be sequentially provided on the preliminary layer PL. In another example embodiment, the reactant RT and the co-reactant CRT may be simultaneously provided on the preliminary layer PL. In still another example embodiment, the reactant RT may be provided on the preliminary layer PL, and thereafter the co-reactant CRT may be sequentially provided on the preliminary layer PL.

The co-reactant CRT may be an organometallic compound containing a second metal M2. The co-reactant CRT may be an organometallic compound represented by Chemical Formula 1 below:

  [Chemical Formula 1]

In Chemical Formula 1, M2 may be selected from the group of Sn, In, and Ge. n may be 2, 3, or 4. In Chemical Formula 1, n may be number of functional groups $L_1$ that are bonded to M2. In an example embodiment, n may be 2, 3, or 4, and thus at least two functional groups $L_1$ may be present.

In an example embodiment, n may correspond to an oxidation number of the second metal M2. For example, when n is 2, the second metal M2 may have an oxidation number of +2, when n is 3, the second metal M2 may have an oxidation number of +3, and when n is 4, the second metal M2 may have an oxidation number of +4.

Each of the $L_1$'s may be the same as or different from each other. $L_1$'s may each independently be hydrogen, halogen, an alkyl group having 1 to 10 carbon atoms, a substituted or unsubstituted amino group, or a substituted or unsubstituted aminoalkyl group. The substituted amino group may be an alkylamino group having 1 to 10 carbon atoms. The substituted aminoalkyl group may be an alkylaminoalkyl group having 2 to 15 carbon atoms.

In an example embodiment, the $L_1$'s may each independently be hydrogen, halogen (F, Cl, Br, or I), or a functional group (or a ligand) represented by Chemical Formula 2 below:

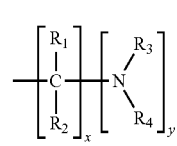  [Chemical Formula 2]

In Chemical Formula 2, x may be 0 or an integer of 1 to 5, and y may be 0 or 1. Where x is 0, y may be 1. $R_1$, $R_2$, $R_3$, and $R_4$ may each independently be hydrogen, an alkyl group having 1 to 5 carbon atoms, or an aminoalkyl group having 1 to 5 carbon atoms. In an example embodiment, a case where y is 0 indicates a hydrogen atom is bonded to the position.

For example, the second metal M2 of the co-reactant CRT may be Sn. Hereinafter, the co-reactant CRT containing Tin (Sn) will be exemplified in detail.

First, when tin (Sn) that is the second metal M2 has an oxidation number of +4, that is, n in Chemical Formula 1 above is 4, specific compounds are exemplified as follows. When n in Chemical Formula 1 is 4, a compound represented by Chemical Formula 1 may have four functional groups (four $L_1$'s) bonded to tin (Sn).

In Chemical Formula 1 above (n=4), four $L_1$'s may each independently be an alkyl group having 1 to 4 carbon atoms (in Chemical Formula 2, x may be an integer of 1 to 4, and y may be 0). In this case, the co-reactant CRT may include a compound represented by Chemical Formula 3 below:

[Chemical Formula 3]

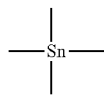

Tetra(methyl)tin

In addition, the co-reactant CRT may include at least one among the following compounds:
Tetra(ethyl)tin;
Tetra(propyl)tin;
Tetra(isopropyl)tin;
Tetra(butyl)tin;
Tetra(sec-butyl)tin;
Dimethyl diethyl tin;
Diethyl diisopropyl tin;
Diisopropyl dimethyl tin;
Dibutyl dimethyl tin;
Tris(isopropyl)methyl tin;
Tris(ethyl)methyl tin;
Tris(methyl)ethyl tin;
Tris(isopropyl)ethyl tin;
Tris(methyl)butyl tin; or
Tris(ethyl)isopropyl tin.

In Chemical Formula 1 above (n=4), four $L_1$'s may each independently be an alkylaminoalkyl group having 2 to 15 carbon atoms (in Chemical Formula 2, x may be an integer of 1 to 4, and y is 1). In this case, the co-reactant CRT may include a compound represented by Chemical Formula 4 below:

[Chemical Formula 4]

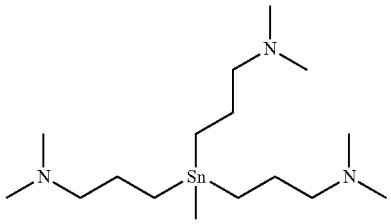

Tetra(3-dimethylaminopropyl) tin

In addition, the co-reactant CRT may include at least one among the following compounds:
Tetra(aminomethyl) tin;
Tetra(2-aminoethyl) tin;
Tetra(3-aminopropyl) tin;
Tetra(dimethylaminomethyl) tin;
Tetra(2-dimethylaminoethyl) tin;
Tetra(3-diethylaminopropyl)tin;
Tetra(3-dimethylamino-2-methylpropyl)tin; or
Tetra(3-diisopropylamino propyl)tin.

In Chemical Formula 1 above (n=4), at least one of four $L_1$'s may be an alkylaminoalkyl group, and at least one of four $L_1$'s may be an alkyl group. In this case, the co-reactant CRT may include a compound represented by Chemical Formula 5 below:

[Chemical Formula 5]

Tris(3-dimethylaminopropyl)methyl tin

In addition, the co-reactant CRT may include at least one among the following compounds:
Tris(aminomethyl)methyl tin;
Tris(aminomethyl)ethyl tin;
Tris(2-aminoethyl)methyl tin;
Tris(2-aminoethyl)ethyl tin;
Tris(3-aminopropyl)methyl tin;
Tris(3-aminopropyl)ethyl tin;
Tris(dimethylaminomethyl)methyl tin;
Tris(dimethylaminomethyl)ethyl tin;
Tris(2-dimethylaminoethyl)methyl tin;
Tris(2-dimethylaminoethyl)ethyl tin;
Tris(3-dimethylaminopropyl)methyl tin;
Tris(3-dimethylaminopropyl)ethyl tin;
Tris(3-diethylaminopropyl)methyl tin;
Tris(3-diethylaminopropyl)ethyl tin;
Bis(aminomethyl)dimethyl tin;
Bis(aminomethyl)diethyl tin;
Bis(2-aminoethyl) dimethyl tin;
Bis(2-aminoethyl) diethyl tin;
Bis(3-aminopropyl) dimethyl tin;
Bis(3-aminopropyl) diethyl tin;
Bis(dimethylaminomethyl) dimethyl tin;
Bis(dimethylaminomethyl) diethyl tin;
Bis(2-dimethylaminoethyl) dimethyl tin;
Bis(2-dimethylaminoethyl) diethyl tin;
Bis(3-diethylaminopropyl)dimethyl tin;
Bis(3-dimethylaminopropyl) diethyl tin;
Bis(3-dimethylaminopropyl)dimethyl tin; or
Bis(3-diethylaminopropyl) diethyl tin.

In Chemical Formula 1 above (n=4), four $L_1$'s may each independently be an alkylamino group having 1 to 10 carbon atoms (in Chemical Formula 2, x may be 0, and y may be 1). In this case, the co-reactant CRT may include a compound represented by Chemical Formula 6 below:

[Chemical Formula 6]

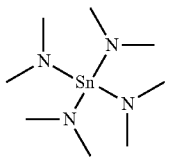

Tetra(dimethyl amino) tin

In addition, the co-reactant CRT may include at least one among the following compounds:
Tetra(amino)tin;
Tetra(diethylamino)tin;
Tetra(ethylmethylamino)tin; or
Tetra(diisopropylamino)tin.

In Chemical Formula 1 above (n=4), at least one of four $L_1$'s may be an alkylamino group, and at least one of four $L_1$'s may be an alkyl group. In this case, the co-reactant CRT may include a compound represented by Chemical Formula 7 below:

[Chemical Formula 7]

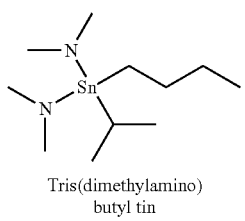

Tris(dimethylamino) butyl tin

In addition, the co-reactant CRT may include at least one among the following compounds:
Tris(amino)methyl tin;
Tris(dimethylamino) methyl tin;
Tris(diethylamino) methyl tin;
Tris(amino)ethyl tin;
Tris(dimethylamino) ethyl tin;
Tris(diethylamino) ethyl tin;
Tris(amino)propyl tin;
Tris(dimethylamino) propyl tin;
Tris(diethylamino) propyl tin;
Tris(amino) butyl tin;
Tris(dimethylamino)butyl tin;
Tris(diethylamino)butyl tin;
Bis(amino)dimethyl tin;
Bis(dimethylamino) dimethyl tin;
Bis(diethylamino) dimethyl tin;
Bis(amino) diethyl tin;
Bis(dimethylamino) diethyl tin;
Bis(diethylamino) diethyl tin;
Bis(amino) dipropyl tin;
Bis(dimethylamino) dipropyl tin;
Bis(diethylamino) dipropyl tin;
Bis(amino) dibutyl tin;
Bis(dimethylamino)dibutyl tin;
Bis(dimethylamino)dibutyl tin;
Bis(diethylamino)dibutyl tin;
Bis(dimethylamino)dimethyl tin;
Bis(diethylamino)dimethyl tin;
Bis(diisopropylamino)dimethyl tin;
Trimethyl (amino) tin;
Trimethyl (dimethylamino) tin;
Trimethyl (diethylamino) tin;
Triethyl (amino) tin;
Triethyl (dimethylamino) tin;
Triethyl (diethylamino) tin;
Tripropyl (amino) tin;
Tripropyl (dimethylamino) tin;
Tripropyl (diethylamino) tin;
Tributyl (amino) tin;
Tributyl(dimethylamino)tin;
Tributyl (diethylamino) tin; or
Tin Tetrahydride tin.

In Chemical Formula 1 above (n=4), at least one of four $L_1$'s may be hydrogen, and the remaining three $L_1$'s may be an alkyl group. In this case, the co-reactant CRT may include a compound represented by Chemical Formula 8 below:

[Chemical Formula 8]

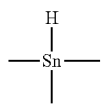

Tri(methyl)tin hydride

In addition, the co-reactant CRT may include at least one among the following compounds:
Tri(methyl)tin hydride;
Tri(ethyl)tin hydride;
Tri(propyl)tin hydride;
Tri(isopropyl)tin hydride;
Tri(butyl)tin hydride;
Tri(sec-butyl)tin hydride;
Dimethyl ethyl tin hydride;
Diethyl isopropyl tin hydride;
Diisopropyl methyl tin hydride;
Dibutyl methyl tin hydride;
Bis(isopropyl)methyl tin hydride;
Bis(ethyl)methyl tin hydride;
Bis(methyl)ethyl tin hydride;
Bis(isopropyl)ethyl tin hydride;
Bis(methyl)butyl tin hydride; or
Bis(ethyl)isopropyl tin hydride.

In Chemical Formula 1 above (n=4), at least one of four $L_1$'s may be hydrogen, and the remaining three $L_1$'s may be an alkylaminoalkyl group. In this case, the co-reactant CRT may include a compound represented by Chemical Formula 9 below:

[Chemical Formula 9]

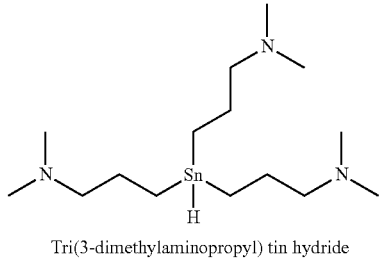

Tri(3-dimethylaminopropyl) tin hydride

In addition, the co-reactant CRT may include at least one among the following compounds:
Tri(3-dimethylaminopropyl)tin hydride;
Tri(3-diethylaminopropyl)tin hydride;
Tri(3-dimethylamino-2-methylpropyl)tin hydride; or
Tri(3-diisopropylamino propyl)tin hydride.

In Chemical Formula 1 above (n=4), at least one of four $L_1$'s may be hydrogen, at least one of four $L_1$'s may be an alkylaminoalkyl group, and at least one of four $L_1$'s may be an alkyl group. In this case, the co-reactant CRT may include a compound represented by Chemical Formula 10 below:

[Chemical Formula 10]

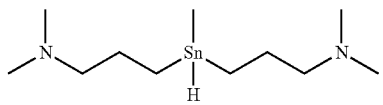

Bis(3-dimethylaminopropyl)methyl tin hydride

In addition, the co-reactant CRT may include at least one among the following compounds:
Bis(3-dimethylaminopropyl)ethyl tin hydride;
Bis(3-diethylaminopropyl)methyl tin hydride;
Bis(3-diethylaminopropyl)ethyl tin hydride;
(3-diethylaminopropyl)dimethyl tin hydride; or
(3-dimethylaminopropyl)dimethyl tin hydride.

In Chemical Formula 1 above (n=4), at least one of four $L_1$'s may be hydrogen, and the remaining three $L_1$'s may be an alkylamino group. In this case, the co-reactant CRT may include a compound represented by Chemical Formula 11 below:

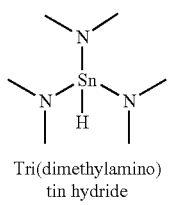

[Chemical Formula 11]

Tri(dimethylamino) tin hydride

In addition, the co-reactant CRT may include at least one among the following compounds:
Tri(diethylamino)tin hydride; or
Tri(ethylmethylamino)tin hydride.

In Chemical Formula 1 above (n=4), at least one of four $L_1$'s may be hydrogen, at least one of four $L_1$'s may be an alkylamino group, and at least one of four $L_1$'s may be an alkyl group. In this case, the co-reactant CRT may include a compound represented by Chemical Formula 12 below:

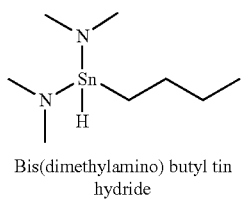

[Chemical Formula 12]

Bis(dimethylamino) butyl tin hydride

In addition, the co-reactant CRT may include at least one among the following compounds:
Bis(diethylamino)butyl tin hydride; or
(dimethylamino)dibutyl tin hydride.

When tin (Sn) that is the second metal M2 has an oxidation number of +3, that is, n in Chemical Formula 1 above is 3, specific compounds are exemplified as follows. When n in Chemical Formula 1 is 3, a compound represented by Chemical Formula 1 may have three functional groups (three $L_1$'s) bonded to tin (Sn).

In Chemical Formula 1 above (n=3), three $L_1$'s may each independently be an alkyl group having 1 to 4 carbon atoms (in Chemical Formula 2, x may be an integer of 1 to 4, and y may be 0). In this case, the co-reactant CRT may include a compound represented by Chemical Formula 13 below:

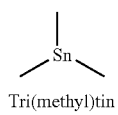

[Chemical Formula 13]

Tri(methyl)tin

In addition, the co-reactant CRT may include at least one among the following compounds:
Tri(ethyl)tin;
Tri(propyl)tin;
Tri(isopropyl)tin;
Tri(butyl)tin;
Tri(sec-butyl)tin;
Dimethyl ethyl tin;
Diethyl isopropyl tin;
Diisopropyl methyl tin;
Dibutyl methyl tin;
Bis(isopropyl)methyl tin;
Bis(ethyl)methyl tin;
Bis(methyl)ethyl tin;
Bis(isopropyl)ethyl tin;
Bis(methyl)butyl tin; or
Bis(ethyl)isopropyl tin.

In Chemical Formula 1 above (n=3), three $L_1$'s may each independently be an alkylaminoalkyl group having 2 to 15 carbon atoms (in Chemical Formula 2, x may be an integer of 1 to 4, and y may be 1). In this case, the co-reactant CRT may include a compound represented by Chemical Formula 14 below:

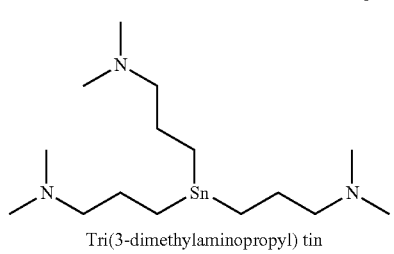

[Chemical Formula 14]

Tri(3-dimethylaminopropyl) tin

In addition, the co-reactant CRT may include at least one among the following compounds:
Tri(3-diethylaminopropyl)tin;
Tri(3-dimethylamino-2-methylpropyl)tin; or
Tri(3-diisopropylamino propyl)tin.

In Chemical Formula 1 above (n=3), at least one of three $L_1$'s may be an alkylaminoalkyl group, and at least one of three $L_1$'s may be an alkyl group. In this case, the co-reactant CRT may include a compound represented by Chemical Formula 15 below:

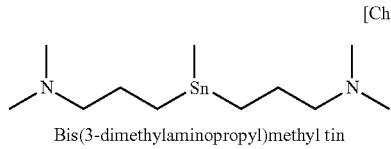

[Chemical Formula 15]

Bis(3-dimethylaminopropyl)methyl tin

In addition, the co-reactant CRT may include at least one among the following compounds:
Bis(3-dimethylaminopropyl)ethyl tin;
Bis(3-diethylaminopropyl)methyl tin;
Bis(3-diethylaminopropyl)ethyl tin;
(3-diethylaminopropyl)dimethyl tin; or
(3-dimethylaminopropyl)dimethyl tin.

In Chemical Formula 1 above (n=3), three $L_1$'s may each independently be an alkylamino group having 1 to 10 carbon atoms (in Chemical Formula 2, x may be 0, and y may be 1).

In this case, the co-reactant CRT may include a compound represented by Chemical Formula 16 below:

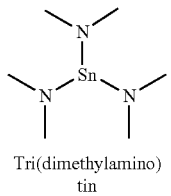

Tri(dimethylamino) tin

[Chemical Formula 16]

In addition, the co-reactant CRT may include at least one among the following compounds:
Tri(diethylamino)tin; or
Tri(ethylmethylamino)tin.

In Chemical Formula 1 above (n=3), at least one of three $L_1$'s may be an alkylamino group, and at least one of three $L_1$'s may be an alkyl group. In this case, the co-reactant CRT may include a compound represented by Chemical Formula 17 below:

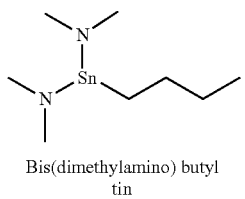

Bis(dimethylamino) butyl tin

[Chemical Formula 17]

In addition, the co-reactant CRT may include at least one among the following compounds:
Bis(diethylamino)butyl tin; or
(dimethylamino)dibutyl tin.

When tin (Sn) that is the second metal M2 has an oxidation number of +2, that is, n in Chemical Formula 1 above is 2, specific compounds are exemplified as follows. When n in Chemical Formula 1 is 2, a compound represented by Chemical Formula 1 may have two functional groups (two $L_1$'s) bonded to tin (Sn).

In Chemical Formula 1 above (n=2), two $L_1$'s may each independently be an alkyl group having 1 to 4 carbon atoms (in Chemical Formula 2, x may be an integer of 1 to 4, and y may be 0). In this case, the co-reactant CRT may include a compound represented by Chemical Formula 18 below:

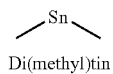

Di(methyl)tin

[Chemical Formula 18]

In addition, the co-reactant CRT may include at least one among the following compounds:
Di(ethyl)tin;
Di(propyl)tin;
Di(isopropyl)tin;
Di(butyl)tin;
Di(sec-butyl)tin;
Ethyl methyl tin;
Ethyl isopropyl tin;
Isopropyl methyl tin;
Butyl methyl tin; or
Ethyl isopropyl tin.

In Chemical Formula 1 above (n=2), two $L_1$'s may each independently be an alkylaminoalkyl group having 2 to 15 carbon atoms (in Chemical Formula 2, x may be an integer of 1 to 4, and y may be 1). In this case, the co-reactant CRT may include a compound represented by Chemical Formula 19 below:

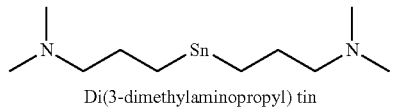

Di(3-dimethylaminopropyl) tin

[Chemical Formula 19]

In addition, the co-reactant CRT may include at least one among the following compounds:
Di(3-diethylaminopropyl)tin;
Di(3-dimethylamino-2-methylpropyl)tin; or
Di(3-diisopropylamino propyl)tin.

In Chemical Formula 1 above (n=2), one of two $L_1$'s may be an alkylaminoalkyl group, and the other of two $L_1$'s may be an alkyl group. In this case, the co-reactant CRT may include a compound represented by Chemical Formula 20 below:

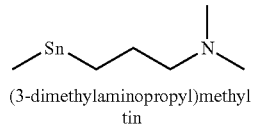

(3-dimethylaminopropyl)methyl tin

[Chemical Formula 20]

In addition, the co-reactant CRT may include at least one among the following compounds:
(3-dimethylaminopropyl)ethyl tin;
(3-diethylaminopropyl)methyl tin; or
(3-diethylaminopropyl)ethyl tin.

In Chemical Formula 1 above (n=2), two $L_1$'s may each independently be an alkylamino group having 1 to 10 carbon atoms (in Chemical Formula 2, x may be 0, and y may be 1). In this case, the co-reactant CRT may include a compound represented by Chemical Formula 21 below:

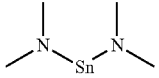

Bis(dimethylamino) tin

[Chemical Formula 21]

In addition, the co-reactant CRT may include at least one among the following compounds:
Bis(diethylamino)tin; or
Bis(ethylmethylamino)tin.

In Chemical Formula 1 above (n=2), one of two $L_1$'s may be an alkylamino group, and the other of two $L_1$'s may be an alkyl group. In this case, the co-reactant CRT may include a compound represented by Chemical Formula 22 below:

[Chemical Formula 22]

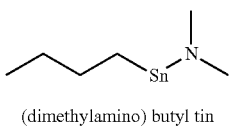

(dimethylamino) butyl tin

In addition, the co-reactant CRT may include the following compound:
(diethylamino)butyl tin.

In another example embodiment, the second metal M2 of the co-reactant CRT may be In. The co-reactant CRT containing indium (In) having an oxidation number of +3 may include the following compounds:

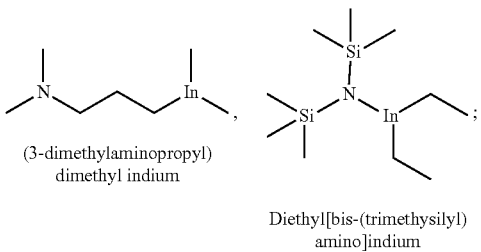

(3-dimethylaminopropyl) dimethyl indium

Diethyl[bis-(trimethysilyl) amino]indium triethyl indium.

The co-reactant CRT containing indium (In) having an oxidation number of +1 may include the following compound:

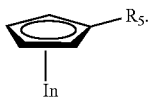

$R_5$ may be hydrogen or an alkyl group having 1 to 5 carbon atoms.

In another example embodiment, the second metal M2 of the co-reactant CRT may be Ge. The co-reactant CRT containing germanium (Ge) having an oxidation number of +4 may include the following compounds:

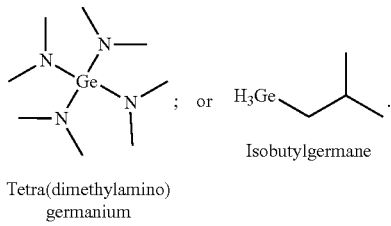

Tetra(dimethylamino) germanium

Isobutylgermane

In Chemical Formula 1 above (n=4), four $L_1$'s may each independently be an alkyl group having 1 to 4 carbon atoms (in Chemical Formula 2, x may be an integer of 1 to 4, and y may be 0). In this case, the co-reactant CRT may include at least one among the following compounds:
Tetra(methyl) germanium;
Tetra(ethyl) germanium;
Tetra(propyl) germanium;
Tetra(isopropyl) germanium;
Tetra(n-butyl) germanium;
Tetra(t-butyl) germanium;
Tetra(sec-butyl)germanium;
Dimethyl diethyl germanium;
Diethyl diisopropyl germanium;
Diisopropyl dimethyl germanium;
Dibutyl dimethyl germanium;
Tris(isopropyl) methyl germanium;
Tris(ethyl) methyl germanium;
Tris(methyl) ethyl germanium;
Tris(isopropyl) ethyl germanium;
Tris(methyl) butyl germanium;
Tris(ethyl) isopropyl germanium;
Digermane; or
Hexamethyl digermanium.

In Chemical Formula 1 above (n=4), four $L_1$'s may each independently be an alkylaminoalkyl group having 2 to 15 carbon atoms (in Chemical Formula 2, x may be an integer of 1 to 4, and y is 1). In this case, the co-reactant CRT may include at least one among the following compounds:
Tetra(aminomethyl) germanium;
Tetra(2-aminoethyl) germanium;
Tetra(3-aminopropyl) germanium;
Tetra(dimethylaminomethyl) germanium;
Tetra(2-dimethylaminoethyl) germanium;
Tetra(3-diethylaminopropyl) germanium;
Tetra(3-dimethylamino-2-methylpropyl) germanium; or
Tetra(3-diisopropylamino propyl) germanium.

In Chemical Formula 1 above (n=4), at least one of four $L_1$'s may be an alkylaminoalkyl group, and at least one of four $L_1$'s may be an alkyl group. In this case, the co-reactant CRT may include at least one among the following compounds:
Tris(aminomethyl)methyl germanium;
Tris(aminomethyl)ethyl germanium;
Tris(2-aminoethyl)methyl germanium;
Tris(2-aminoethyl)ethyl germanium;
Tris(3-aminopropyl)methyl germanium;
Tris(3-aminopropyl)ethyl germanium;
Tris(dimethylaminomethyl)methyl germanium;
Tris(dimethylaminomethyl)ethyl germanium;
Tris(2-dimethylaminoethyl)methyl germanium;
Tris(2-dimethylaminoethyl)ethyl germanium;
Tris(3-dimethylaminopropyl)methyl germanium;
Tris(3-dimethylaminopropyl)ethyl germanium;
Tris(3-diethylaminopropyl)methyl germanium;
Tris(3-diethylaminopropyl)ethyl germanium;
Bis(aminomethyl)dimethyl germanium;
Bis(aminomethyl)diethyl germanium;
Bis(2-aminoethyl) dimethyl germanium;
Bis(2-aminoethyl) diethyl germanium;
Bis(3-aminopropyl) dimethyl germanium;
Bis(3-aminopropyl) diethyl germanium;
Bis(dimethylaminomethyl) dimethyl germanium;
Bis(dimethylaminomethyl) diethyl germanium;
Bis(2-dimethylaminoethyl) dimethyl germanium;
Bis(2-dimethylaminoethyl) diethyl germanium;
Bis(3-dimethylaminopropyl)dimethyl germanium;
Bis(3-dimethylaminopropyl) diethyl germanium;
Bis(3-diethylaminopropyl)dimethyl germanium; or
Bis(3-diethylaminopropyl) diethyl germanium.

In Chemical Formula 1 above (n=4), four $L_1$'s may each independently be an alkylamino group having 1 to 10 carbon atoms (in Chemical Formula 2, x may be 0, and y may be 1). In this case, the co-reactant CRT may include at least one among the following compounds:
Tetraamino germanium;
Tetra(diethylamino) germanium;

Tetra(ethylmethylamino) germanium; or
Tetra(diisopropylamino) germanium.

In Chemical Formula 1 above (n=4), at least one of four $L_1$'s may be an alkylamino group, and at least one of four $L_1$'s may be an alkyl group. In this case, the co-reactant CRT may include at least one among the following compounds:

Tris(amino)methyl germanium;
Tris(dimethylamino) methyl germanium;
Tris(diethylamino) methyl germanium;
Tris(amino)ethyl germanium;
Tris(dimethylamino) ethyl germanium;
Tris(diethylamino) ethyl germanium;
Tris(amino)propyl germanium;
Tris(dimethylamino) propyl germanium;
Tris(diethylamino) propyl germanium;
Tris(amino) butyl germanium;
Tris(dimethylamino) butyl germanium;
Tris(diethylamino) butyl germanium;
Bis(amino)dimethyl germanium;
Bis(dimethylamino) dimethyl germanium;
Bis(diethylamino) dimethyl germanium;
Bis(amino) diethyl germanium;
Bis(dimethylamino) diethyl germanium;
Bis(diethylamino) diethyl germanium;
Bis(amino) dipropyl germanium;
Bis(dimethylamino) dipropyl germanium;
Bis(diethylamino) dipropyl germanium;
Bis(amino) dibutyl germanium;
Bis(dimethylamino) dibutyl germanium;
Bis(diethylamino) dibutyl germanium;
Trimethyl (amino) germanium;
Trimethyl (dimethylamino) germanium;
Trimethyl (diethylamino) germanium;
Triethyl (amino) germanium;
Triethyl (dimethylamino) germanium;
Triethyl (diethylamino) germanium;
Tripropyl (amino) germanium;
Tripropyl (dimethylamino) germanium;
Tripropyl (diethylamino) germanium;
Tributyl (amino) germanium;
Tributyl (dimethylamino) germanium; or
Tributyl (diethylamino) germanium.

In Chemical Formula 1 above (n=4), at least one of four $L_1$'s may be hydrogen, and the remaining three $L_1$'s may be an alkyl group. In this case, the co-reactant CRT may include at least one among the following compounds:

Tri(methyl)germanium hydride;
Tri (ethyl)germanium hydride;
Tri (propyl)germanium hydride;
Tri (isopropyl)germanium hydride;
Tri (butyl)germanium hydride;
Tri (sec-butyl)germanium hydride;
Dimethyl ethyl germanium hydride;
Diethyl isopropyl germanium hydride;
Diisopropyl methyl germanium hydride;
Dibutyl methyl germanium hydride;
Bis(isopropyl) methyl germanium hydride;
Bis (ethyl) methyl germanium hydride;
Bis(methyl) ethyl germanium hydride;
Bis (isopropyl) ethyl germanium hydride;
Bis(methyl) butyl germanium hydride; or
Bis (ethyl) isopropyl germanium hydride.

In Chemical Formula 1 above (n=4), at least two of four $L_1$'s may be hydrogen, and the remaining $L_1$'s may be an alkyl group. In this case, the co-reactant CRT may include at least one among the following compounds:

Dimethylgermanium dihydride;
Diethylgermanium dihydride;
Dipropylgermanium dihydride;
Diisopropylgermanium dihydride;
Dibutylgermanium dihydride;
Di(sec-butyl)germanium dihydride;
methylgermanium trihydride;
ethylgermanium trihydride;
propylgermanium trihydride;
isopropylgermanium trihydride;
butylgermanium trihydride;
(sec-butyl)germanium trihydride; or
Germanium tetrahydride.

In Chemical Formula 1 above (n=4), at least one of four $L_1$'s may be hydrogen, and the remaining three $L_1$'s may be an alkylaminoalkyl group. In this case, the co-reactant CRT may include at least one among the following compounds:

Tris(aminomethyl) germanium hydride;
Tris(2-aminoethyl) germanium hydride;
Tris(3-aminopropyl) germanium hydride;
Tris(dimethylaminomethyl) germanium hydride;
Tris(2-dimethylaminoethyl)methyl germanium hydride;
Tris(3-dimethylaminopropyl) germanium hydride;
Tris(3-diethylaminopropyl) germanium hydride;
Tris (3-dimethylamino-2-methylpropyl) germanium hydride;
Tris (3-diisopropylamino propyl) germanium hydride;
Bis(aminomethyl) germanium dihydride;
Bis(2-aminoethyl) germanium dihydride;
Bis(3-aminopropyl) germanium dihydride;
Bis(dimethylaminomethyl) germanium dihydride;
Bis(2-dimethylaminoethyl) germanium dihydride;
Bis(3-dimethylaminopropyl)germanium dihydride;
Bis(3-diethylaminopropyl) germanium dihydride;
Bis(3-dimethylamino-2-methylpropyl) germanium dihydride;
Bis(3-diisopropylamino propyl) germanium dihydride;
(aminomethyl) germanium trihydride;
(2-aminoethyl) germanium trihydride;
(3-aminopropyl) germanium trihydride;
(dimethylaminomethyl) germanium trihydride;
(2-dimethylaminoethyl) germanium trihydride;
(3-dimethylaminopropyl) germanium trihydride;
(3-diethylaminopropyl) germanium trihydride;
(3-dimethylamino-2-methylpropyl) germanium trihydride; or
(3-diisopropylamino propyl) germanium trihydride.

In Chemical Formula 1 above (n=4), at least one of four $L_1$'s may be hydrogen, at least one of four $L_1$'s may be an alkylaminoalkyl group, and at least one of four $L_1$'s may be an alkyl group. In this case, the co-reactant CRT may include at least one among the following compounds:

Bis(amino)methyl germanium hydride;
Bis(dimethylamino) methyl germanium hydride;
Bis(diethylamino) methyl germanium hydride;
Bis(amino)ethyl germanium hydride;
Bis(dimethylamino) ethyl germanium hydride;
Bis(diethylamino) ethyl germanium hydride;
Bis(amino)propyl germanium hydride;
Bis(dimethylamino) propyl germanium hydride;
Bis(diethylamino) propyl germanium hydride;
Bis(amino) butyl germanium hydride;
Bis(dimethylamino) butyl germanium hydride;
Bis(diethylamino) butyl germanium hydride;

Bis(3-dimethylaminopropyl)methyl germanium hydride;
Bis(3-dimethylaminopropyl)ethyl germanium hydride;
Bis(3-diethylaminopropyl)methyl germanium hydride;
Bis(3-diethylaminopropyl)ethyl germanium hydride;
(amino)dimethyl germanium hydride;
(dimethylamino) dimethyl germanium hydride;
(diethylamino) dimethyl germanium hydride;
(amino) diethyl germanium hydride;
(dimethylamino) diethyl germanium hydride;
(diethylamino) diethyl germanium hydride;
(amino) dipropyl germanium hydride;
(dimethylamino) dipropyl germanium hydride;
(diethylamino) dipropyl germanium hydride;
(amino) dibutyl germanium hydride;
(dimethylamino) dibutyl germanium hydride;
(diethylamino) dibutyl germanium hydride;
(3-dimethylaminopropyl) dimethyl germanium hydride;
(3-dimethylaminopropyl) diethyl germanium hydride;
(3-diethylaminopropyl) dimethyl germanium hydride;
(3-diethylaminopropyl) diethyl germanium hydride;
(amino)methyl germanium dihydride;
(dimethylamino) methyl germanium dihydride;
(diethylamino) methyl germanium dihydride;
(amino) ethyl germanium dihydride;
(dimethylamino) ethyl germanium dihydride;
(diethylamino) ethyl germanium dihydride;
(amino) propyl germanium dihydride;
(dimethylamino) propyl germanium dihydride;
(diethylamino) propyl germanium dihydride;
(amino) butyl germanium dihydride;
(dimethylamino) butyl germanium dihydride;
(diethylamino) butyl germanium dihydride;
(3-dimethylaminopropyl) methyl germanium dihydride;
(3-dimethylaminopropyl) ethyl germanium dihydride;
(3-diethylaminopropyl) methyl germanium dihydride; or
(3-diethylaminopropyl) ethyl germanium dihydride.

In Chemical Formula 1 above (n=4), at least one of four $L_1$'s may be hydrogen, and the remaining three $L_1$'s may be an alkylamino group. In this case, the co-reactant CRT may include at least one among the following compounds:
Triamino germanium hydride;
Tris(diethylamino) germanium hydride;
Tris(ethylmethylamino) germanium hydride;
Tris(diisopropylamino) germanium hydride;
Diamino germanium dihydride;
Bis(diethylamino) germanium dihydride;
Bis(ethylmethylamino) germanium dihydride;
Bis(diisopropylamino) germanium dihydride
amino germanium trihydride;
(diethylamino) germanium trihydride;
(ethylmethylamino) germanium trihydride; or
(diisopropylamino) germanium trihydride.

In Chemical Formula 1 above (n=4), at least one of four $L_1$'s may be hydrogen, at least one of four $L_1$'s may be an alkylamino group, and at least one of four $L_1$'s may be an alkyl group. In this case, the co-reactant CRT may include at least one among the following compounds:
Dimethyl (amino) germanium hydride;
Dimethyl (dimethylamino) germanium hydride;
Dimethyl (diethylamino) germanium hydride;
Diethyl (amino) germanium hydride;
Diethyl (dimethylamino) germanium hydride;
Diethyl (diethylamino) germanium hydride;
Diisopropyl (amino) germanium hydride;
Diisopropyl (dimethylamino) germanium hydride;
Diisopropyl (diethylamino) germanium hydride;
Dibutyl (amino) germanium hydride;
Dibutyl (dimethylamino) germanium hydride;
Dibutyl (diethylamino) germanium hydride;
Bis (amino) methyl germanium hydride;
Bis (dimethylamino) methyl germanium hydride;
Bis (diethylamino) methyl germanium hydride;
Bis (amino) ethylgermanium hydride;
Bis (dimethylamino) ethylgermanium hydride;
Bis (diethylamino) ethyl germanium hydride;
Bis (amino) isopropyl germanium hydride;
Bis (dimethylamino) isopropyl germanium hydride;
Bis (diethylamino) isopropyl germanium hydride;
Bis (amino) butyl germanium hydride;
Bis (dimethylamino) butyl germanium hydride; or
Bis(diethylamino) butyl germanium hydride.

When germanium (Ge) that is the second metal M2 has an oxidation number of +3, that is, n in Chemical Formula 1 above is 3, specific compounds are exemplified as follows. When n in Chemical Formula 1 is 3, a compound represented by Chemical Formula 1 may have three functional groups (three $L_1$'s) bonded to germanium (Ge).

In Chemical Formula 1 above (n=3), three $L_1$'s may each independently be an alkyl group having 1 to 4 carbon atoms (in Chemical Formula 2, x may be an integer of 1 to 4, and y may be 0). In this case, the co-reactant CRT may include at least one among the following compounds:
Tri (ethyl)germanium;
Tri (propyl)germanium;
Tri (isopropyl)germanium;
Tri (butyl)germanium;
Tri (sec-butyl)germanium;
Dimethyl ethyl germanium;
Diethyl isopropyl germanium;
Diisopropyl methyl germanium;
Dibutyl methyl germanium;
Bis(isopropyl) methyl germanium;
Bis (ethyl) methyl germanium;
Bis(methyl) ethyl germanium;
Bis (isopropyl) ethyl germanium;
Bis(methyl) butyl germanium; or
Bis (ethyl) isopropyl germanium.

In Chemical Formula 1 above (n=3), three $L_1$'s may each independently be an alkylaminoalkyl group having 2 to 15 carbon atoms (in Chemical Formula 2, x may be an integer of 1 to 4, and y may be 1). In this case, the co-reactant CRT may include at least one among the following compounds:
Tri (3-diethylaminopropyl) germanium;
Tri (3-dimethylamino-2-methylpropyl) germanium; or
Tri (3-diisopropylamino propyl) germanium.

In Chemical Formula 1 above (n=3), at least one of three $L_1$'s may be an alkylaminoalkyl group, and at least one of three $L_1$'s may be an alkyl group. In this case, the co-reactant CRT may include at least one among the following compounds:
Bis(3-dimethylaminopropyl)ethyl germanium;
Bis(3-diethylaminopropyl)methyl germanium;
Bis(3-diethylaminopropyl)ethyl germanium;
(3-diethylaminopropyl)dimethyl germanium; or
(3-dimethylaminopropyl)dimethyl germanium.

In Chemical Formula 1 above (n=3), three $L_1$'s may each independently be an alkylamino group having 1 to 10 carbon atoms (in Chemical Formula 2, x may be 0, and y may be 1). In this case, the co-reactant CRT may include at least one among the following compounds:
Tri(diethylamino) germanium; or
Tri(ethylmethylamino) germanium.

In Chemical Formula 1 above (n=3), at least one of three $L_1$'s may be an alkylamino group, and at least one of three $L_1$'s may be an alkyl group. In this case, the co-reactant CRT may include at least one among the following compounds:

Bis(diethylamino) butyl germanium; or (dimethylamino) dibutyl germanium.

When germanium (Ge) that is the second metal M2 has an oxidation number of +2, that is, n in Chemical Formula 1 above is 2, specific compounds are exemplified as follows. When n in Chemical Formula 1 is 2, a compound represented by Chemical Formula 1 may have two functional groups (two $L_1$'s) bonded to germanium (Ge).

In Chemical Formula 1 above (n=2), two $L_1$'s may each independently be an alkyl group having 1 to 4 carbon atoms (in Chemical Formula 2, x may be an integer of 1 to 4, and y may be 0). In this case, the co-reactant CRT may include at least one among the following compounds:

Di (ethyl)germanium;

Di (propyl)germanium;

Di (isopropyl)germanium;

Di (butyl)germanium;

Di (sec-butyl)germanium;

Ethyl methyl germanium;

Ethyl isopropyl germanium;

Isopropyl methyl germanium;

Butyl methyl germanium; or

Ethyl isopropyl germanium.

In Chemical Formula 1 above (n=2), two $L_1$'s may each independently be an alkylaminoalkyl group having 2 to 15 carbon atoms (in Chemical Formula 2, x may be an integer of 1 to 4, and y may be 1). In this case, the co-reactant CRT may include at least one among the following compounds:

Di (3-diethylaminopropyl) germanium;

Di (3-dimethylamino-2-methylpropyl) germanium; or

Di (3-diisopropylamino propyl) germanium.

In Chemical Formula 1 above (n=2), one of two $L_1$'s may be an alkylaminoalkyl group, and the other of two $L_1$'s may be an alkyl group. In this case, the co-reactant CRT may include at least one among the following compounds:

(3-dimethylaminopropyl)ethyl germanium;

(3-diethylaminopropyl)methyl germanium; or (3-diethylaminopropyl)ethyl germanium.

In Chemical Formula 1 above (n=2), two $L_1$'s may each independently be an alkylamino group having 1 to 10 carbon atoms (in Chemical Formula 2, x may be 0, and y may be 1). In this case, the co-reactant CRT may include at least one among the following compounds:

Bis(diethylamino) germanium; or

Bis(ethylmethylamino) germanium.

In Chemical Formula 1 above (n=2), one of two $L_1$'s may be an alkylamino group, and the other of two $L_1$'s may be an alkyl group. In this case, the co-reactant CRT may include the following compound:

(diethylamino) butyl germanium.

The co-reactant CRT containing germanium (Ge) having an oxidation number of +2 may include at least one among the following compounds:

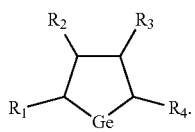

R1 to R4 may each independently be hydrogen or an alkyl group having 1 to 5 carbon atoms.

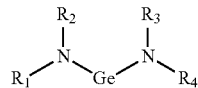

R1 to R4 may each independently be hydrogen, an alkyl group having 1 to 5 carbon atoms, or an alkylsilyl group having 1 to 10 carbon atoms.

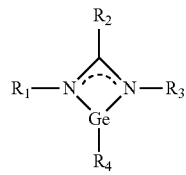

R1 and R3 may each independently be hydrogen or an alkyl group having 1 to 5 carbon atoms. R2 and R4 may each independently be an alkylamino group having 1 to 10 carbon atoms, or an alkyl group having 1 to 5 carbon atoms.

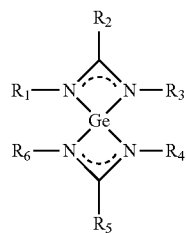

R1 to R6 may each independently be hydrogen or an alkyl group having 1 to 5 carbon atoms.

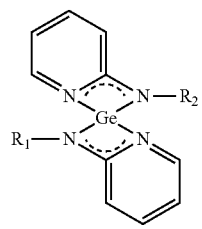

R1 and R2 may each independently be an alkylsilyl group having 1 to 10 carbon atoms.

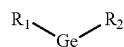

R1 and R2 may each independently be an alkylsilyl group having 1 to 10 carbon atoms.

Referring to FIG. 7, the preliminary layer PL and the reactant RT may react with each other and the first metal M1 may be reduced to form a metal-containing layer ML. The metal-containing layer ML may be a metal nitride layer containing the first metal M1. The metal nitride layer may have a relatively low resistivity, and thus may be substantially a conductor.

Byproducts of the reduction reaction and the oxidized co-reactant CRT may all be removed. Thus, the second metal M2 of the co-reactant CRT may not remain and may all be removed in the metal-containing layer ML. The removal of the byproducts and the co-reactant CRT may include purging gases from a process chamber. As described above, the co-reactant CRT may serve as a catalyst in the formation reaction of the metal-containing layer ML.

In an example embodiment, the metal-containing layer ML may not include the second metal M2. In another example embodiment, while the preliminary layer PL is reduced, the second metal M2 of the co-reactant CRT may diffuse into the preliminary layer PL, and the metal-containing layer ML may include a slight amount of the second metal M2. In this case, a content of the second metal M2 in the metal-containing layer ML may be, for example, about 0.1 at % to about 10 at %.

As described above in the comparative example, if the metal-containing layer is formed using the reduction reaction without the co-reactant CRT, a process temperature of about 500° C. or higher may be used. In contrast, with respect to the method of forming a metal nitride layer according to an example embodiment, the co-reactant CRT may promote the reduction of the preliminary layer PL even at low temperatures (e.g., between about 150° C. and 400° C.). The method according to an example embodiment may be performed at low temperatures, and thus a lower layer formed in a preceding step may not be damaged. Therefore, the reliability of the semiconductor device may be improved.

A method of forming a metal nitride layer according to an example embodiment may have excellent step coverage characteristics due to not using plasma, and thus may be used in regions having a high aspect ratio. Further, according to an example embodiment, a safer reactant such as ammonia may be used instead of using a reactant having a strong reactivity, and a metal nitride layer may be formed at low temperatures.

According to another example embodiment, a process for forming a metal-containing layer ML may be performed at a process temperature of about 400° C. to about 600° C. In this case, electronic characteristics of a metal-containing layer (i.e., a metal nitride layer) may exhibit further reduced resistivity.

According to still another example embodiment, the reactant RT in FIG. 6 may not contain a nitrogen atom. Thus, the reactant RT may not be a nitrogen source. For example, the reactant RT may be hydrogen ($H_2$). In this case, the metal-containing layer ML may be formed with a metal layer (e.g., a titanium layer, a tantalum layer, a cobalt layer, a tungsten layer, a ruthenium layer, a molybdenum layer, a tin layer, a copper layer, an iridium layer or a vanadium layer) composed of only the first metal M1.

Experimental Example

As a Comparative Example, as described above with reference to FIGS. 1 to 3, $TiCl_4$ was used as the metal precursor MP, and $NH_3$ was used as the reactant RT, and thereby a TiN layer was deposited through the ALD process. The process temperature was about 450° C.

As an Example, as described above with reference to FIGS. 5 to 7, $TiCl_4$ was used as the metal precursor MP, a compound represented by Chemical Formula 7 below was used as the co-reactant CRT, and $NH_3$ was used as the reactant RT, and thereby a TiN layer was deposited through the ALD process. The process temperature was about 350° C.

[Chemical Formula 7]

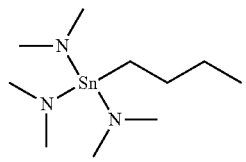

Tri(dimethylamino) butyl tin

As a result of performing XPS analysis of a TiN layer formed according to the Example, an atomic percent of Ti was about 48 at %, and an atomic percent of N was about 46 at %. Thus, it was confirmed that the ratio of the number of Ti atoms to the number of N atoms in the TiN layer was about 1:1, and Ti of the TiN layer had an oxidation number of +3. The atomic ratio of N to Ti of the TiN layer formed according to an example embodiment may be 0.9 to 1.1.

Figure 8:
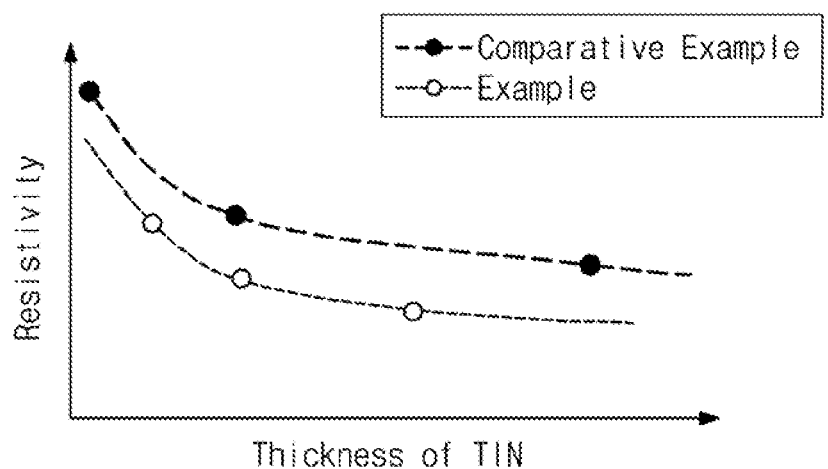
FIG. 8 is a graph in which the resistivity of a TiN layer according to an example embodiment and the resistivity of a TiN layer according to a comparative example are measured.
Figure 9:
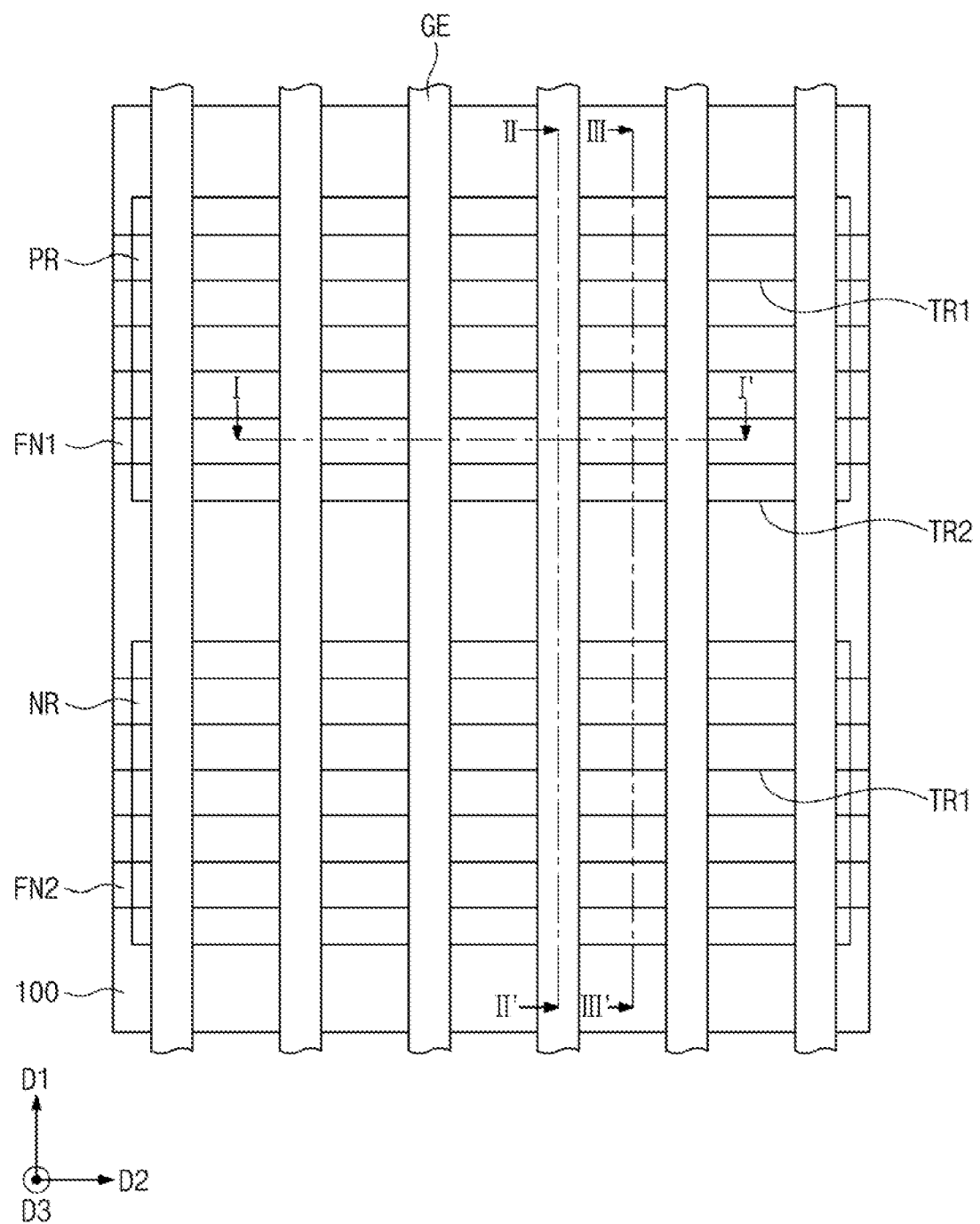
FIGS. 9, 11, 13, and 15 illustrate plan views of stages in a method of manufacturing a semiconductor device according to an example embodiment.
Figure 10A:
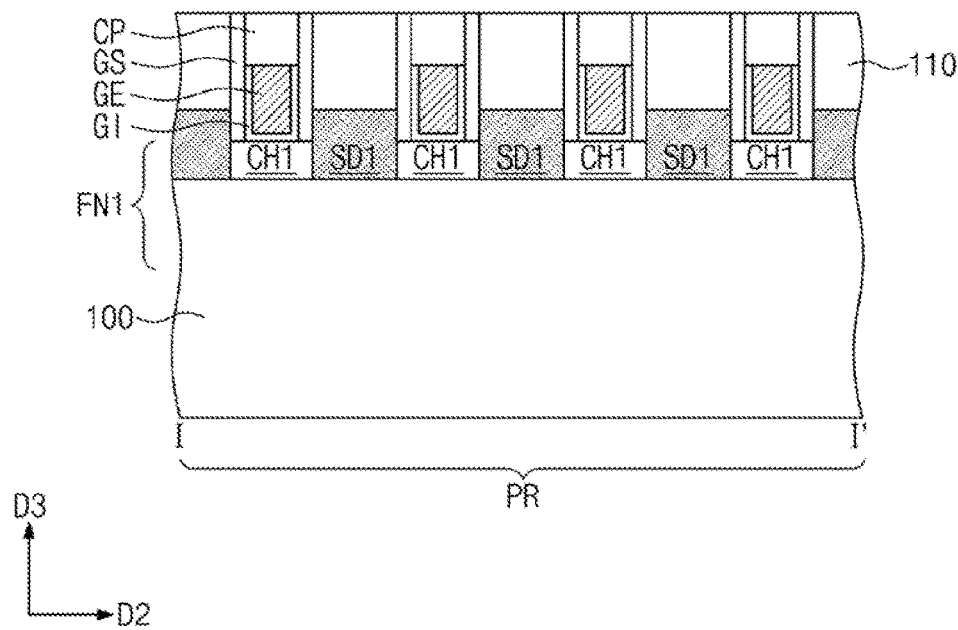
FIGS. 10A, 12A, 14A, and 16A illustrate cross-sectional views taken along line I-I' of FIGS. 9, 11, 13, and 15, respectively.
Figure 10B:
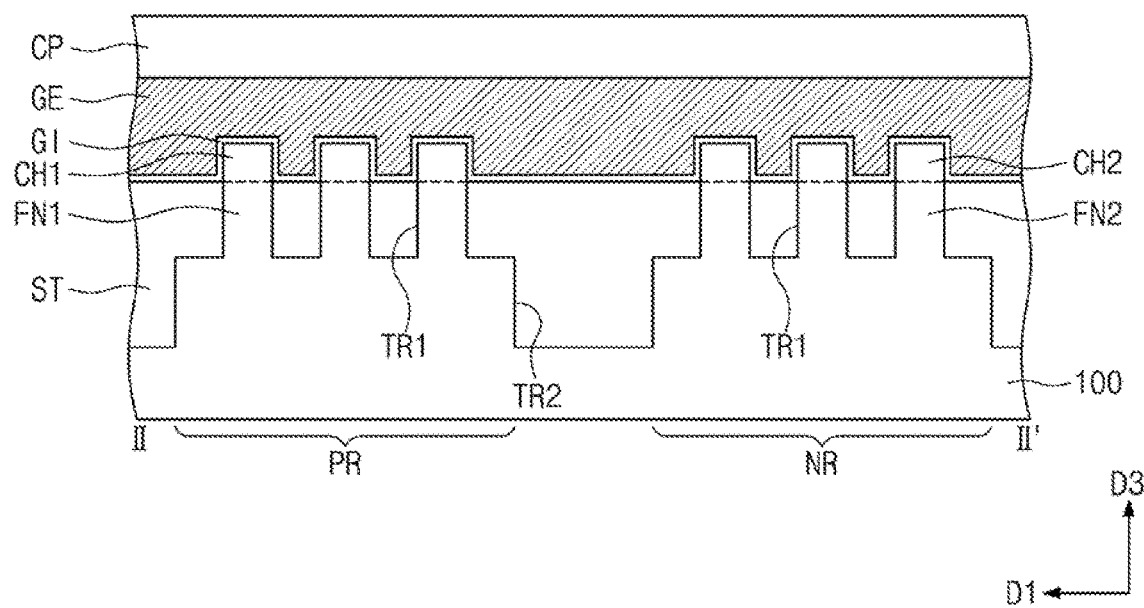
Figure 10C:
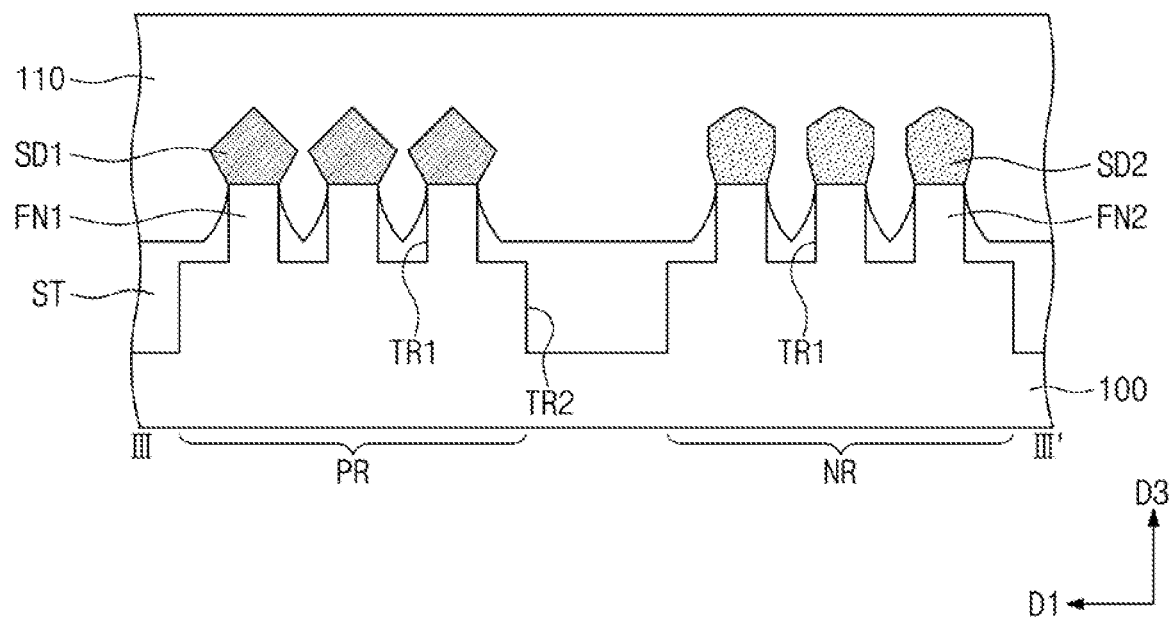
FIGS. 10C, 12C, 14C, and 16C illustrate cross-sectional views taken along line III-III' of FIGS. 9, 11, 13, and 15, respectively.
Figure 11:
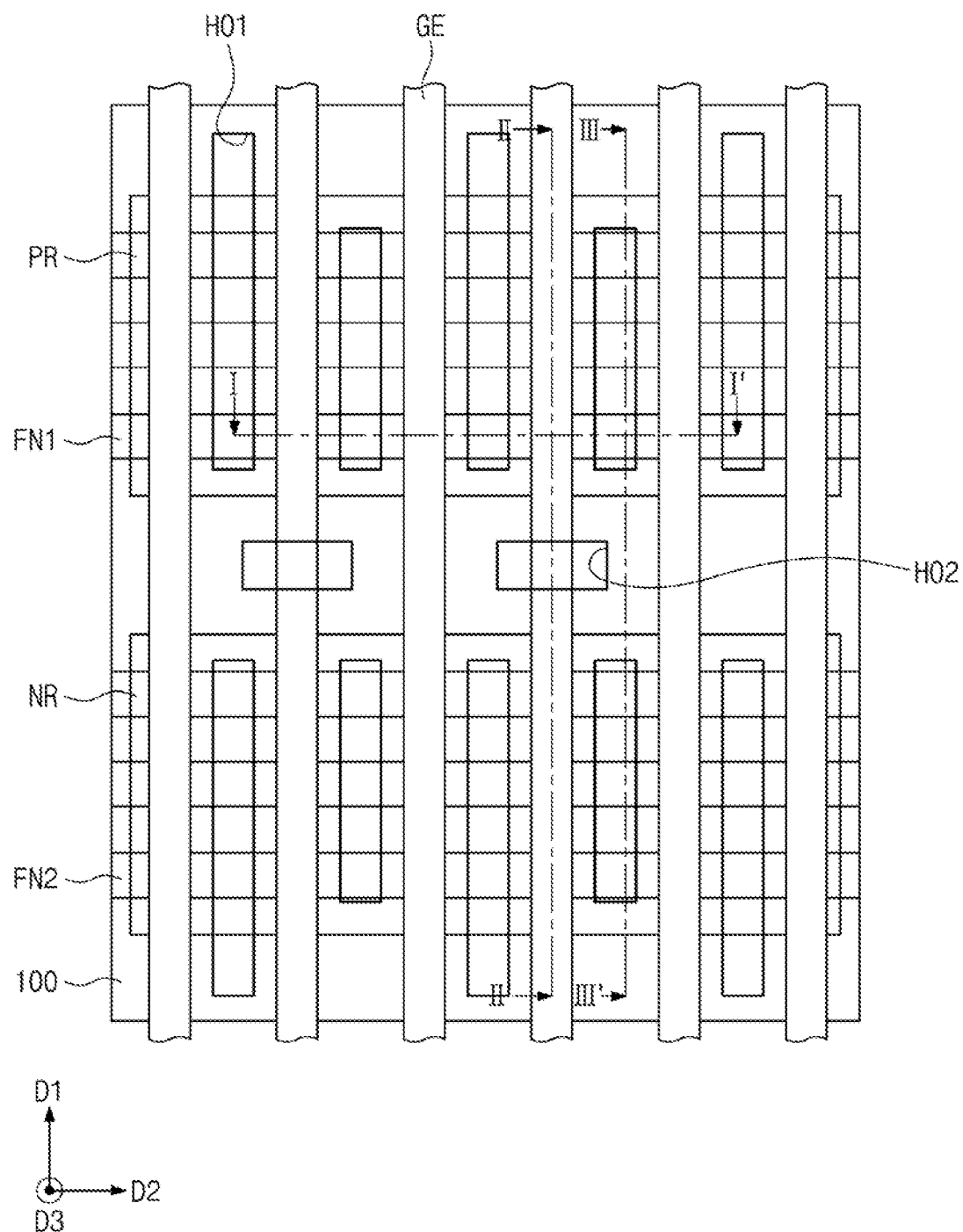
Figure 12A:
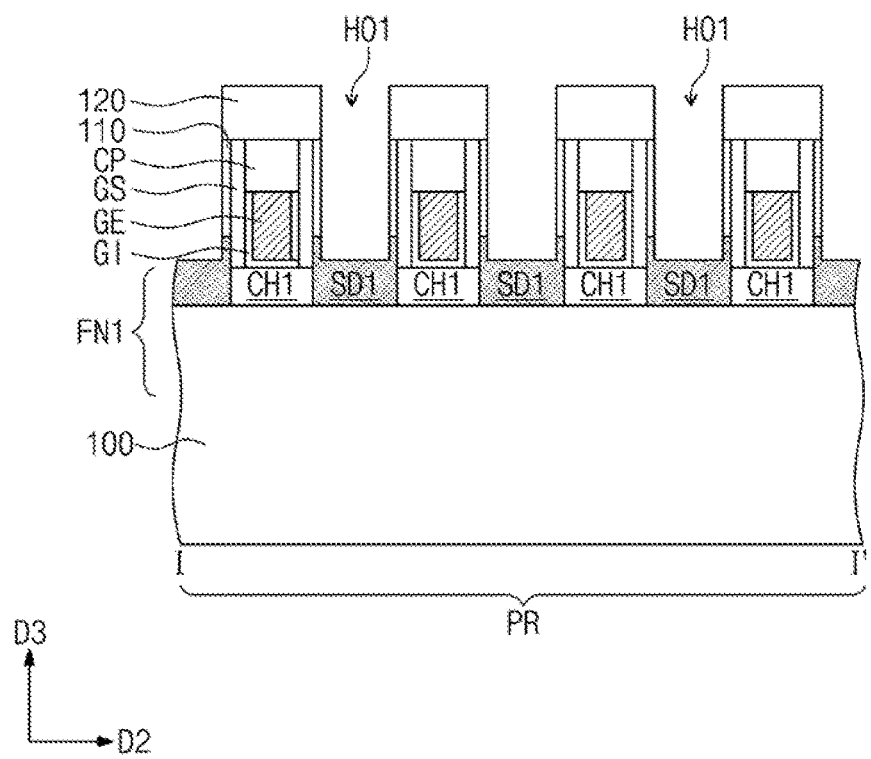
Figure 12B:
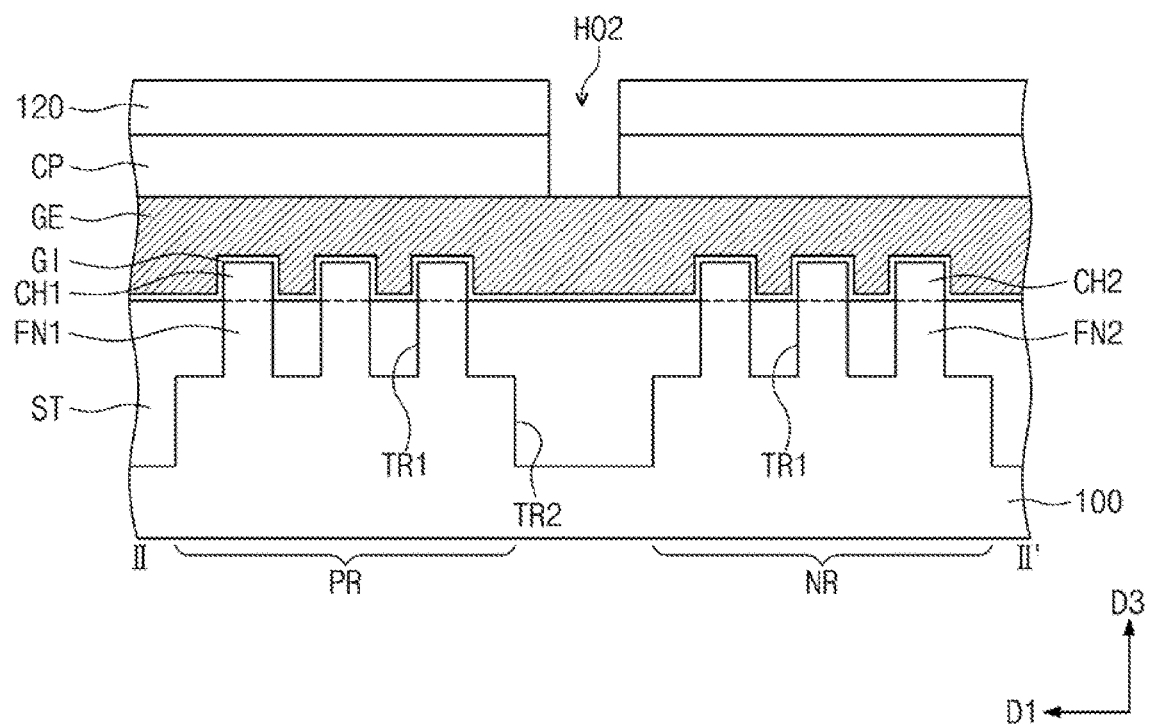
Figure 12C:
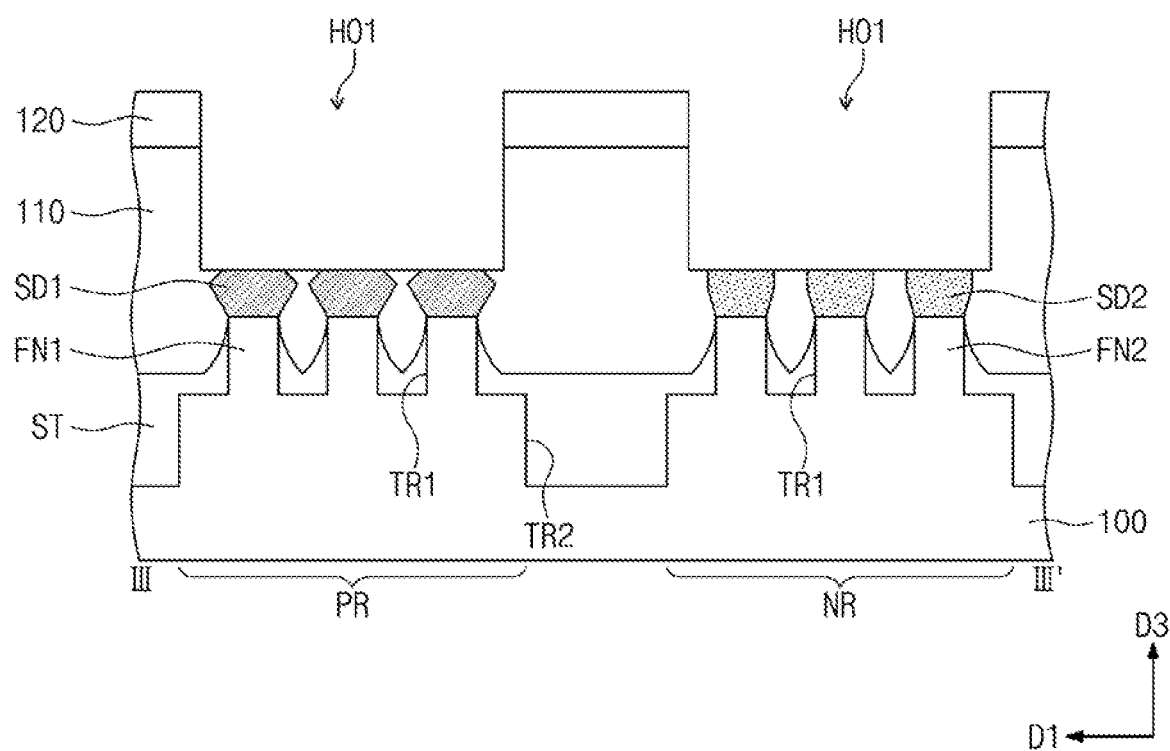
Figure 13:
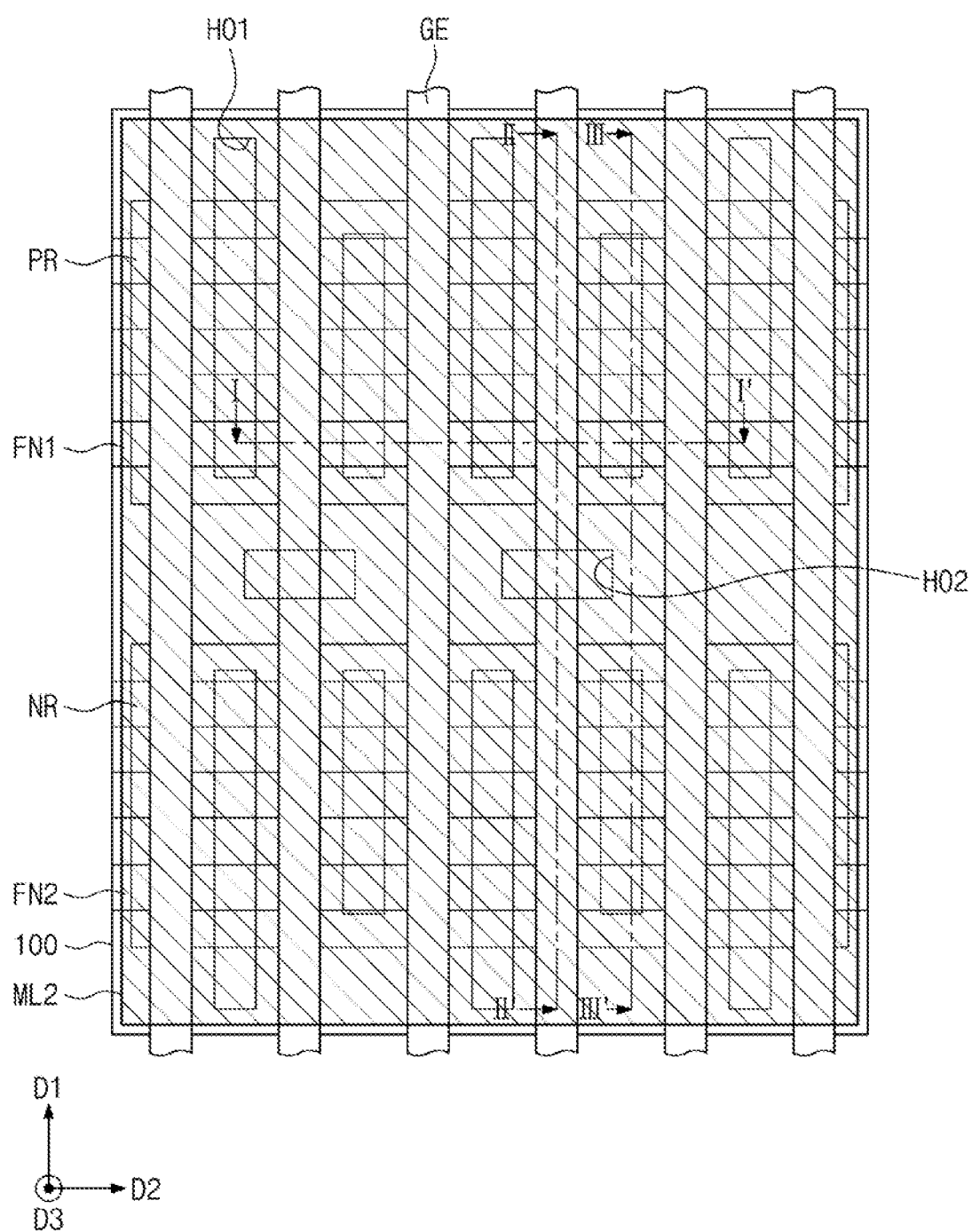
Figure 14A:
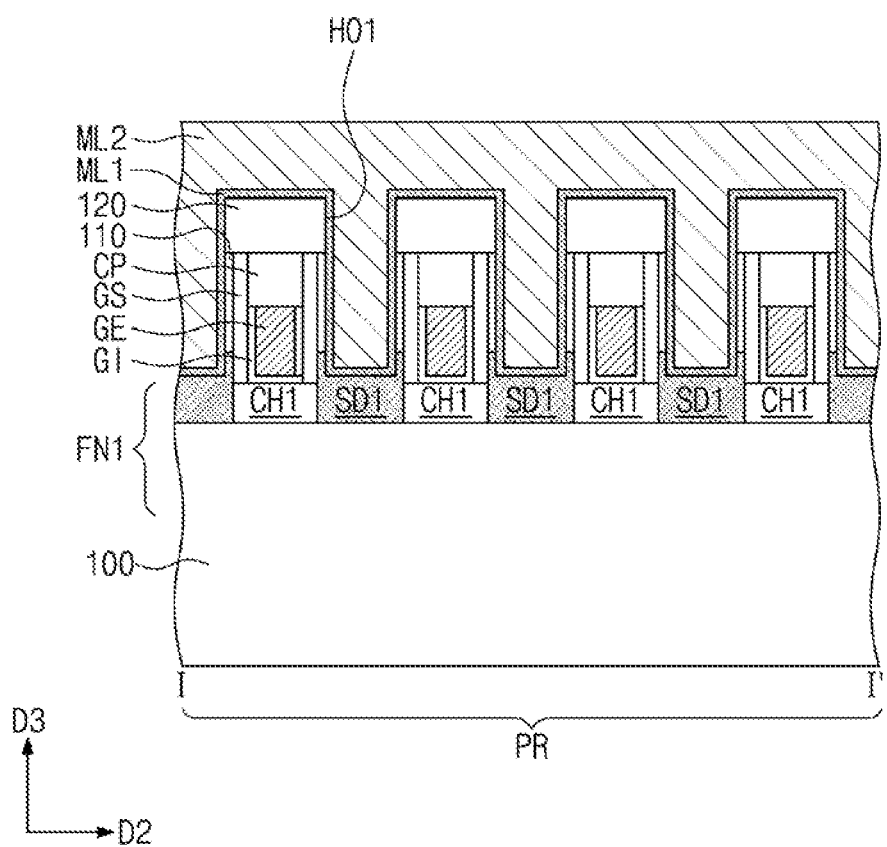
Figure 14B:
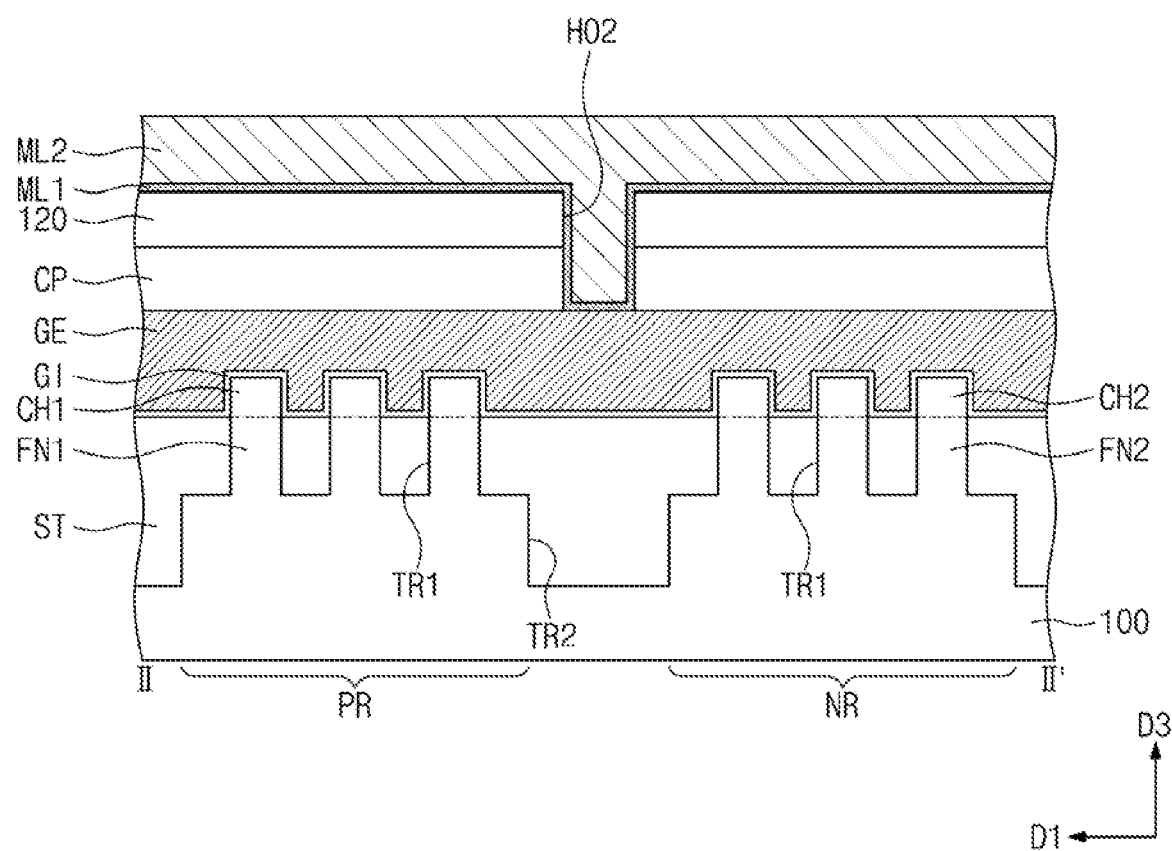
Figure 14C:
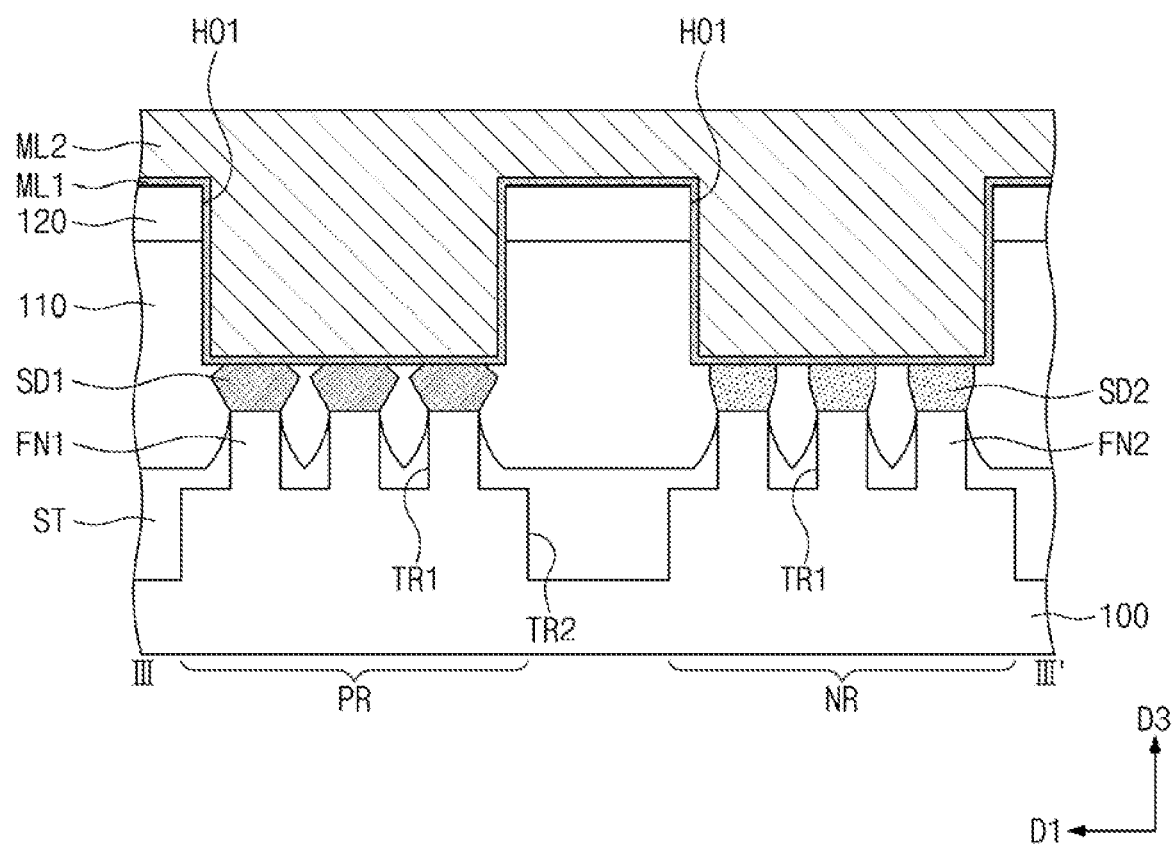
Figure 15:
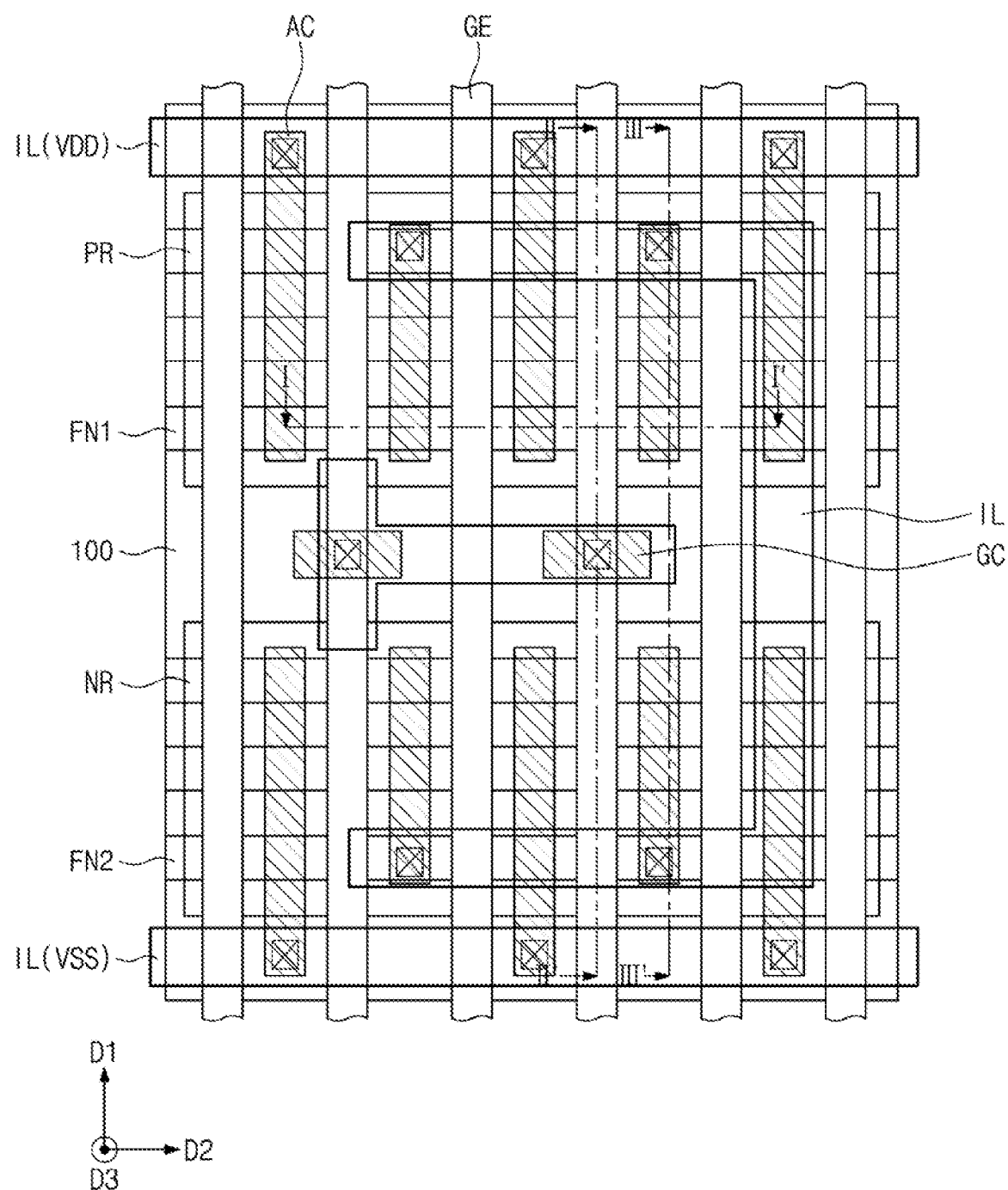
Figure 16A:
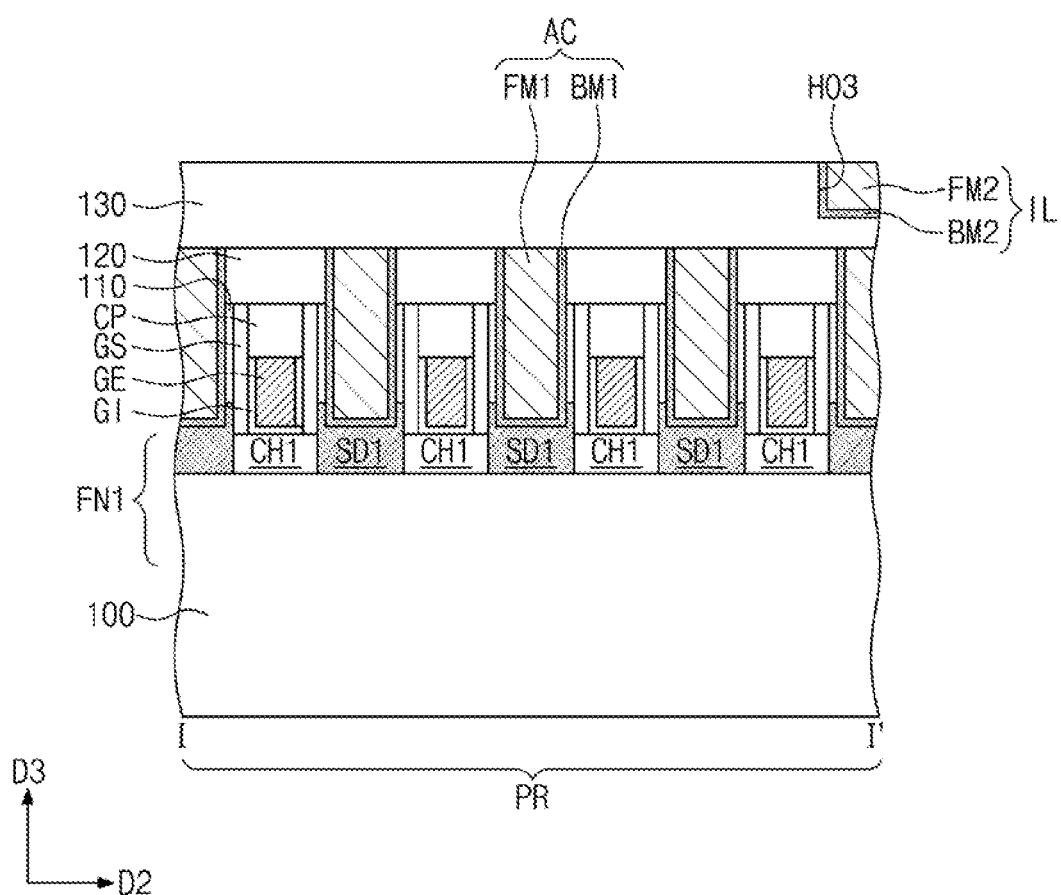
Figure 16C:
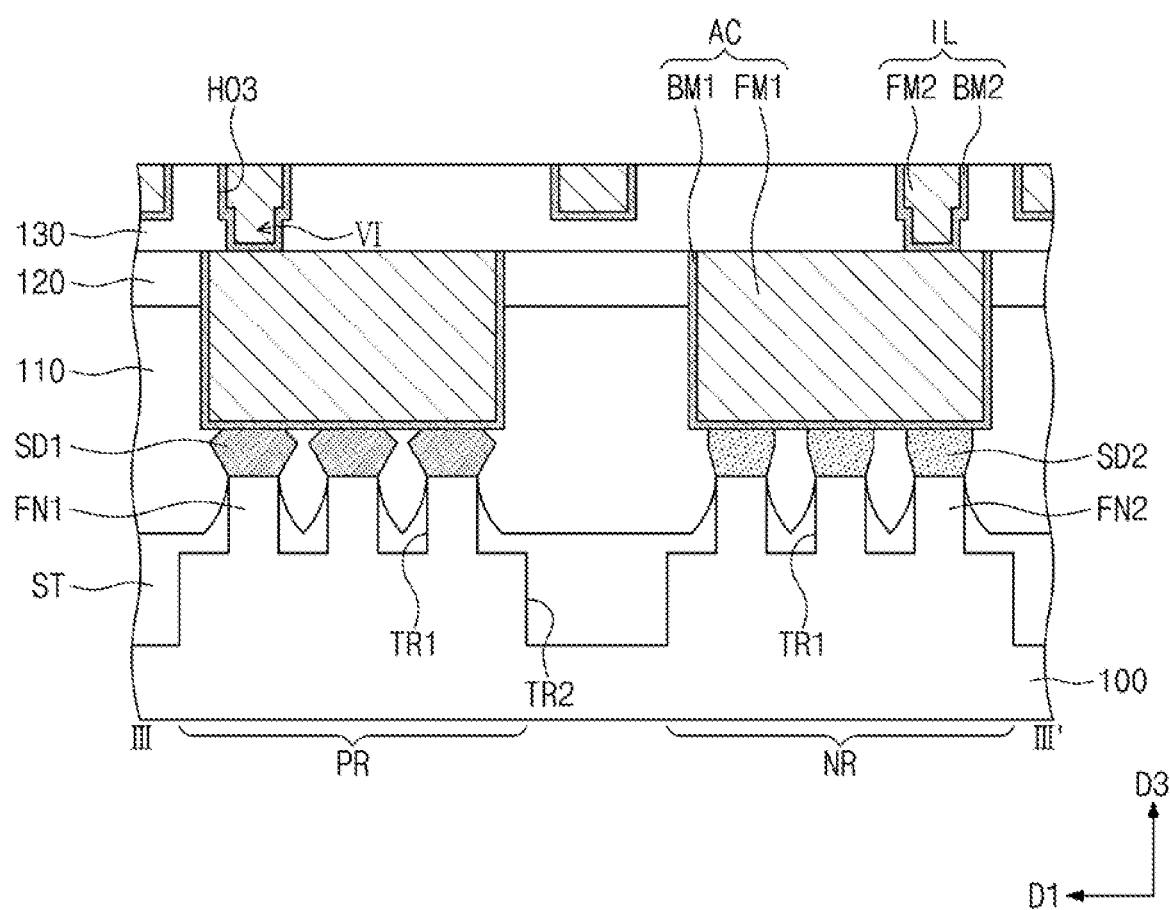

The results of measuring resistivity with respect to the TiN layer formed according to the Comparative Example and the TiN layer formed according to the Examples are shown in FIG. 8.

Referring to FIG. 8, it can be seen that the resistivity of the TiN layer according to the Example is lower than that of the TiN layer according to the Comparative Example. Although the TiN layer according to the Example was deposited at a low temperature (350° C.), the resistivity of the TiN layer according to the Example was lower than that of the TiN layer deposited at a high temperature (450° C.) according to the Comparative Example. Thus, it can be seen that the TiN layer according to the Example was reduced better than the TiN layer according to the Comparative Example. This indicates that when the co-reactant according to an example embodiment is used, the reduction reaction between $TiCl_4$ and $NH_3$ is actively performed even at low temperatures.

FIGS. 9, 11, 13, and 15 illustrate plan views of stages in a method of manufacturing a semiconductor device according to an example embodiment. FIGS. 10A, 12A, 14A, and 16A illustrate cross-sectional views taken along line I-I' of FIGS. 9, 11, 13, and 15, respectively. FIGS. 10B, 12B, 14B, and 16B illustrate cross-sectional views taken along line II-II' of FIGS. 9, 11, 13, and 15, respectively. FIGS. 10C, 12C, 14C, and 16C illustrate cross-sectional views taken along line III-III' of FIGS. 9, 11, 13, and 15, respectively.

Referring to FIGS. 9 and 10A to 10C, a substrate 100 may be provided. For example, the substrate 100 may be a silicon substrate, a germanium substrate, or a silicon-on-insulator (SOI) substrate. An upper portion of the substrate 100 may be patterned to form first trenches TR1 extending in a second direction D2. The first trenches TR1 may define first and second active patterns FN1 and FN2 on the upper portion of the substrate 100. The first and second active patterns FN1 and FN2 may be arranged along a first direction D1.

An upper portion of the substrate 100 may be patterned to form second trenches TR2 defining a first active region PR and a second active region NR. While the second trenches TR2 are formed, the first and second active patterns FN1 and FN2 may be removed from an area in which the second trench TR2 is formed. The first active pattern FN1 may be provided on the first active region PR, and the second active pattern FN2 may be provided on the second active region NR. The second trenches TR2 may be deeper than the first trenches TR1.

A device isolation layer ST may be formed to fill the first and second trenches TR1 and TR2. Silicon oxide may be used to form the device isolation layer ST. For example, the formation of the device isolation layer ST may include forming on the substrate 100 a dielectric layer that fills the first and second trenches TR1 and TR2, and recessing the dielectric layer until the first and second active patterns FN1 and FN2 are exposed on their upper portions.

Gate electrodes GE may be formed to extend in the first direction D1, while running across the first and second active patterns FN1 and FN2. Gate dielectric layers GI may be formed below the gate electrodes GE. Gate spacers GS may be formed on opposite sides of each of the gate electrodes GE. Gate capping layers CP may be formed on the gate electrodes GE.

The formation of the gate electrodes GE may include forming sacrificial patterns to run across the first and second active patterns FN1 and FN2, forming the gate spacers GS on opposite sides of each of the sacrificial patterns, and replacing the sacrificial patterns with the gate electrodes GE.

The gate electrodes GE may include a conductive metal nitride (e.g., titanium nitride or tantalum nitride) or a (non-compounded) metal (e.g., titanium, tantalum, cobalt, tungsten, ruthenium, molybdenum, tin, copper, or aluminum). The formation of the gate electrodes GE may include the formation of the metal-containing layer ML discussed above with reference to FIGS. 5 to 7 according to an example embodiment.

The gate dielectric layers GI may include a high-k dielectric material whose dielectric constant is greater than that of a silicon oxide layer. The gate spacers GS may include at least one of SiCN, SiCON, or SiN. The gate capping layers CP may include at least one of SiON, SiCN, SiCON, or SiN.

First source/drain regions SD1 may be formed on upper portions of the first active patterns FN1. Second source/drain regions SD2 may be formed on upper portions of the second active patterns FN2. The first and second source/drain regions SD1 and SD2 may be formed on opposite sides of each of the gate electrodes GE. The first source/drain regions SD1 may be doped with p-type impurities, and the second source/drain regions SD2 may be doped with n-type impurities.

The first and second source/drain regions SD1 and SD2 may be epitaxial patterns, which epitaxial patterns may be formed by a selective epitaxial growth process. For example, a partial recess process may be performed on the first and second active patterns FN1 and FN2 on opposite sides of each of the gate electrodes GE, and then an epitaxial growth process may be performed on the recessed portions of the first and second active patterns FN1 and FN2.

A first interlayer dielectric layer 110 may be formed on an entire surface of the substrate 100. The first interlayer dielectric layer 110 may be formed of a silicon oxide layer or a silicon oxynitride layer. The first interlayer dielectric layer 110 may have a top surface substantially coplanar with those of the gate spacers GS and those of the gate capping layers CP.

Referring to FIGS. 11 and 12A to 12C, a second interlayer dielectric layer 120 may be formed on the first interlayer dielectric layer 110. First holes HO1 may be formed to penetrate the first and second interlayer dielectric layers 110 and 120. Second holes HO2 may be formed to penetrate the second interlayer dielectric layer 120 and the gate capping layers CP.

Each of the first holes HO1 may be formed between adjacent gate electrodes GE. Each of the first holes HO1 may expose the first source/drain region SD1 or the second source/drain region SD2. The second holes HO2 may be formed on the device isolation layer ST filling the second trenches TR2. Each of the second holes HO2 may expose at least a portion of a top surface of the gate electrode GE.

Referring to FIGS. 13 and 14A to 14C, a first metal-containing layer ML1 and a second metal-containing layer ML2 may be formed to sequentially fill the first and second holes HO1 and HO2. The first metal-containing layer ML1 may be conformally formed on the substrate 100. The first metal-containing layer ML1 may include a metal nitride layer, for example, a titanium nitride layer, a tungsten nitride layer, or a tantalum nitride layer. The formation of the first metal-containing layer ML1 may include the formation of the metal-containing layer ML described above with reference to FIGS. 5 to 7 according to an example embodiment.

The first and second holes HO1 and HO2 may have a relatively high aspect ratio. If plasma is used in the deposition process to form the first metal-containing layer ML1, plasma may provide poor step coverage characteristics, and thus it may be difficult to conformally form the first metal-containing layer ML1 in the first and second holes HO1 and HO2. However, the method of forming the metal-containing layer according to the present example embodiment may conformally form the first metal-containing layer ML1 in the first and second holes HO1 and HO2 without using plasma.

The second metal-containing layer ML2 may be formed on the first metal-containing layer ML1. The second metal-containing layer ML2 may include a metal layer containing, for example, titanium, tantalum, cobalt, tungsten, ruthenium, molybdenum, tin, copper, or aluminum. The formation of the second metal-containing layer ML2 may include the formation of the metal-containing layer ML discussed above with reference to FIGS. 5 to 7 according to an example embodiment. The second metal-containing layer ML2 may completely fill the first and second holes HO1 and HO2.

At least one of the first metal-containing layer ML1 or the second metal-containing layer ML2 may contain the second metal M2 of the co-reactant CRT described above with reference to FIGS. 5 to 7. A content of the second metal M2 contained in at least one of the first metal-containing layer ML1 or the second metal-containing layer ML2 may be, for example, about 0.1 at % to about 10 at %.

Referring to FIGS. 15 and 16A to 16C, a planarization process may be performed on the first metal-containing layer ML1 and the second metal-containing layer ML2 until a top surface of the second interlayer dielectric layer 120 is exposed, and accordingly, active contacts AC and gate contacts GC may be formed respectively in the first holes HO1 and the second holes HO2. Each of the active contact AC and the gate contact GC may include a first barrier pattern BM1 and a first conductive pattern FM1.

A third interlayer dielectric layer 130 may be formed on the second interlayer dielectric layer 120. The third interlayer dielectric layer 130 may be patterned to form third holes HO3 in the third interlayer dielectric layer 130.

Interconnection lines IL may be formed to fill the third holes HO3. Each of the interconnection lines IL may include a second barrier pattern BM2 and a second conductive pattern FM2.

The formation of the interconnection lines IL may include forming a third metal-containing layer on the substrate 100 and forming a fourth metal-containing layer on the third metal-containing layer. The formation of the third and fourth metal-containing layers may include the formation of the metal-containing layer ML discussed above with reference to FIGS. 5 to 7 according to an example embodiment. In an example embodiment, the third metal-containing layer may include a metal nitride layer, and the fourth metal-containing layer may include a metal layer. The third and fourth metal-containing layers may undergo a planarization process to form the second barrier pattern BM2 and the second conductive pattern FM2.

At least one of the interconnection lines IL may include a via VI. The interconnection line IL may be electrically connected through the via VI to one or more of the active contacts AC and the gate contacts GC.

Figure 17:
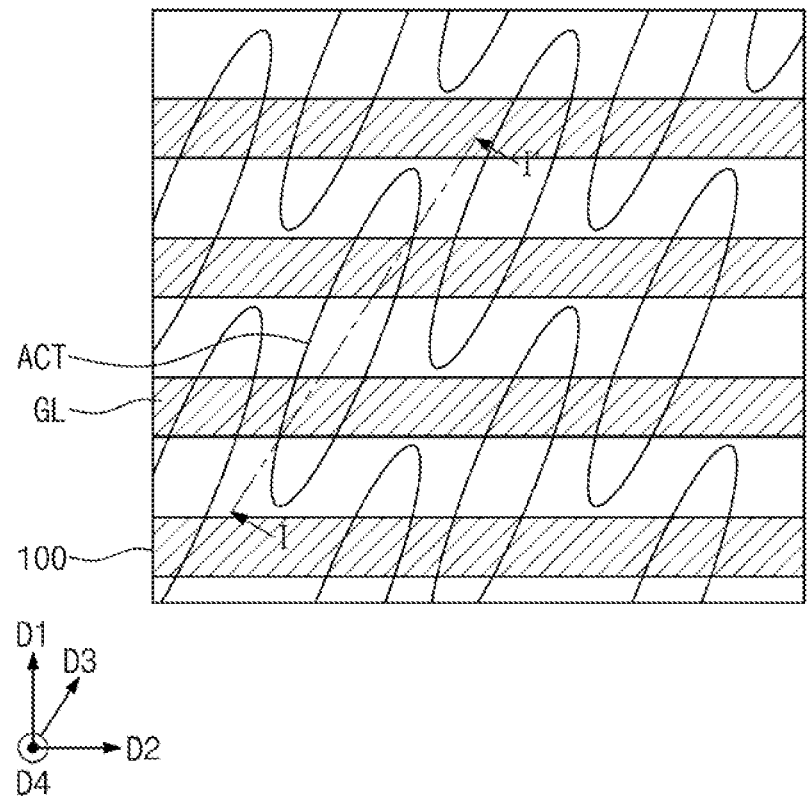
FIGS. 17 and 19 illustrate plan views of stages in a method of manufacturing a semiconductor device according to an example embodiment.
Figure 18:
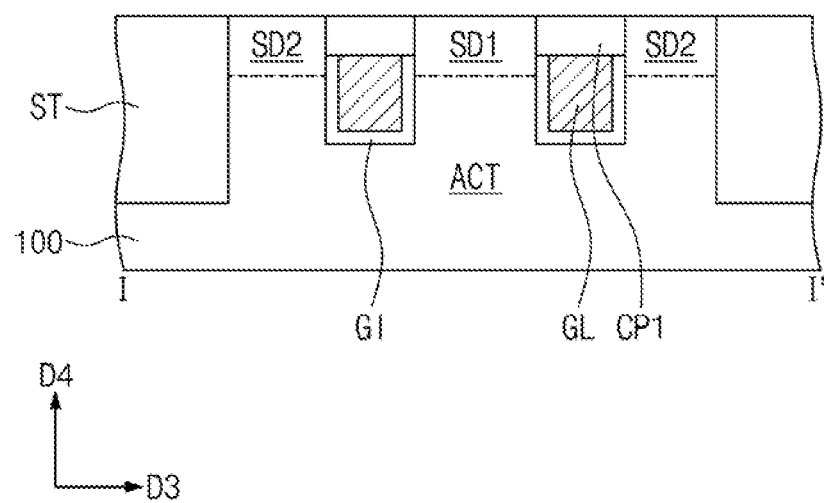
FIGS. 18 and 20 illustrate cross-sectional views taken along line I-I' of FIGS. 17 and 19, respectively.
Figure 19:
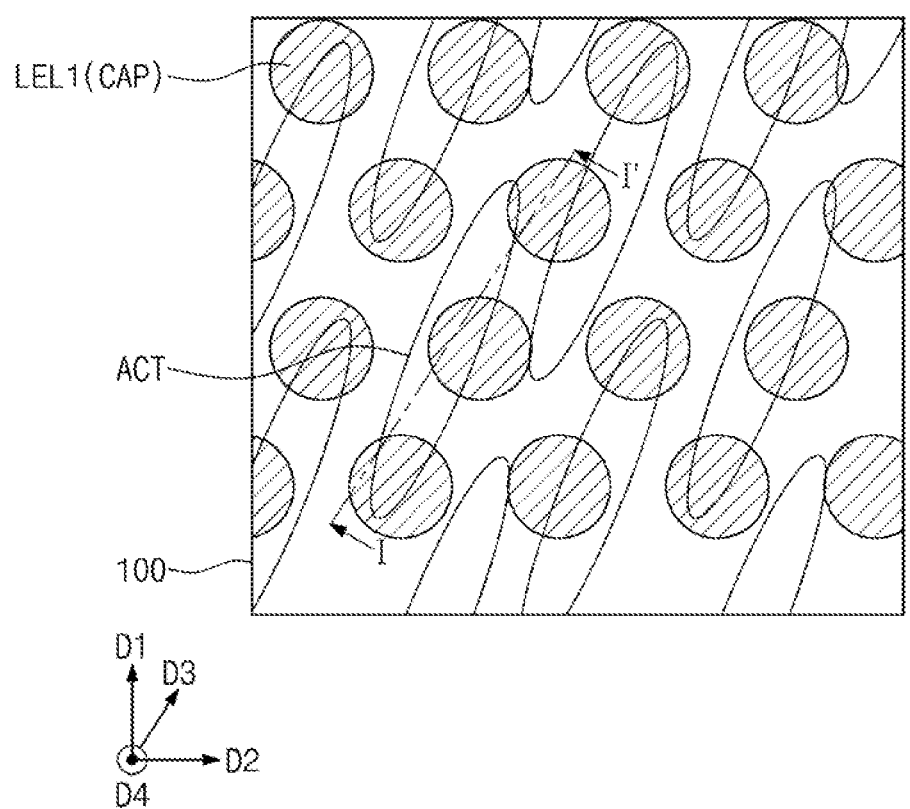
Figure 20:
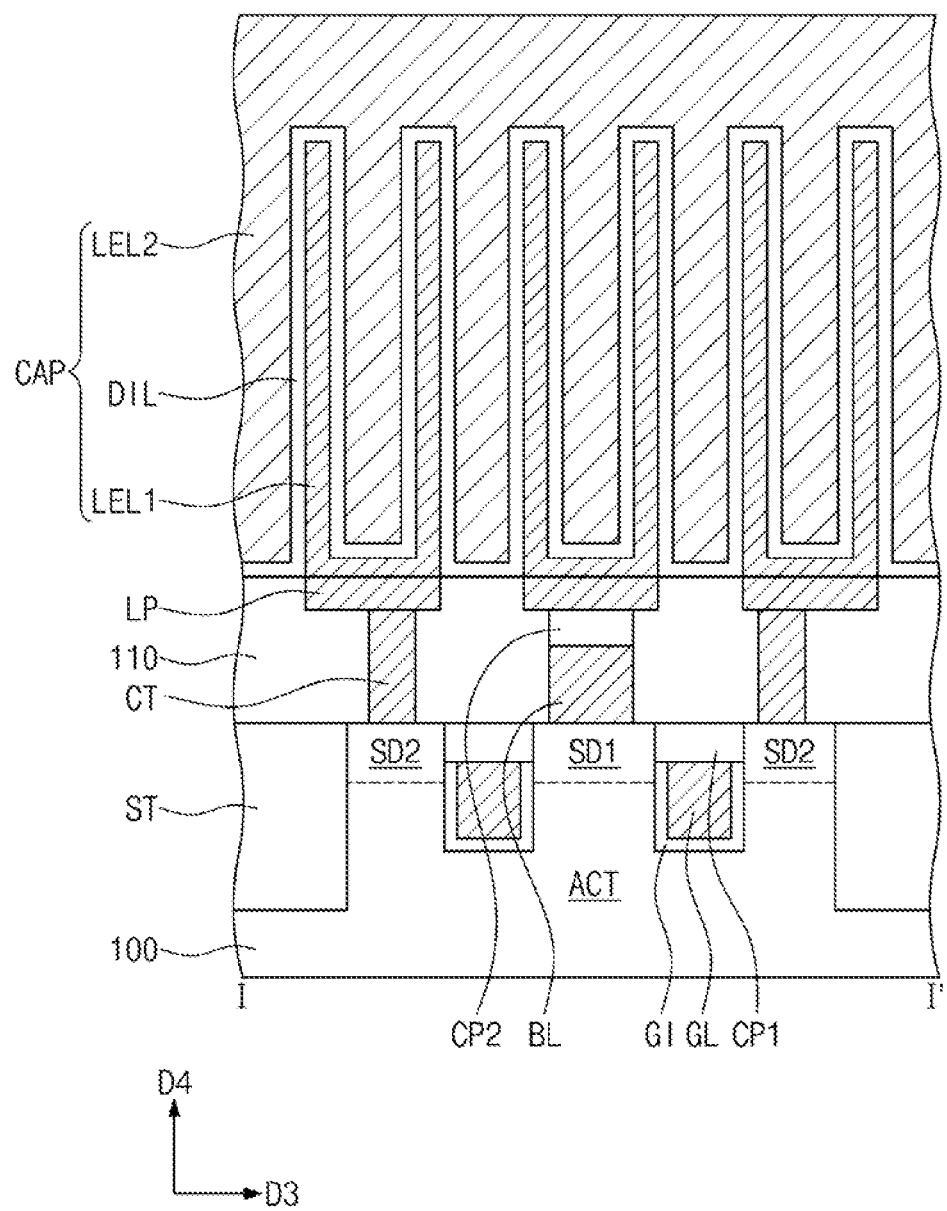

FIGS. 17 and 19 illustrate plan views of stages in a method of manufacturing a semiconductor device according to an example embodiment. FIGS. 18 and 20 illustrate cross-sectional views taken along line I-I' of FIGS. 17 and 19, respectively.

Referring to FIGS. 17 and 18, a substrate 100 may be provided thereon with a device isolation layer ST defining active patterns ACT. The substrate 100 may be, for example, a silicon substrate, a germanium substrate, or a silicon-on-insulator (SOI) substrate. Silicon oxide may be used to form the device isolation layer ST.

When viewed in plan, each of the active patterns ACT may have a bar shape. Each of the active patterns ACT may have a major axis in a third direction D3. A third direction D3 may intersect first and second directions D1 and D2. The first, second, and third directions D1, D2 and D3 may all be parallel to a top surface of the substrate 100.

Gate lines GL may be formed in the substrate 100, running across the active patterns ACT. The gate lines GL may extend in the second direction D2 and may be arranged along the first direction D1. The gate lines GL may be formed to be buried in the substrate 100.

The gate lines GL may include, for example, a conductive metal nitride (e.g., titanium nitride or tantalum nitride) or a (non-compounded) metal (e.g., titanium, tantalum, cobalt, tungsten, ruthenium, molybdenum, tin, copper, or aluminum). The formation of the gate lines GL may include the formation of the metal-containing layer ML described above with reference to FIGS. 5 to 7 according to an example embodiment.

Gate dielectric layers GI may be formed between the gate lines GL and the active patterns ACT. The gate dielectric layers GI may include a high-k dielectric material whose dielectric constant is greater than that of a silicon oxide layer.

First capping patterns CP1 may be formed on corresponding gate lines GL. The first capping patterns CP1 may have top surfaces that are substantially coplanar with that of the substrate 100. In an example embodiment, the first capping patterns CP1 may contain at least one of SiON, SiCN, SiCON, or SiN.

A first source/drain region SD1 may be formed on each of the active patterns ACT, and on the each of the active patterns ACT, second source/drain regions SD2 may be formed spaced apart from each other across the first source/drain region SD1. The first source/drain region SD1 may be formed between a pair of gate lines GL neighboring each other. The second source/drain regions SD2 may be formed on opposite sides of the pair of gate lines GL. For example, the second source/drain regions SD2 may be spaced apart from each other across the pair of gate lines GL. The first source/drain region SD1 may have the same conductive type as that of the second source/drain region SD2.

Referring to FIGS. 19 and 20, a first interlayer dielectric layer 110 may be formed on the substrate 100, covering the active patterns ACT. The first interlayer dielectric layer 110 may be formed of a silicon oxide layer or a silicon oxynitride layer.

Bit lines BL may be formed in the first interlayer dielectric layer 110. The bit lines BL may extend in the first direction D1 and may be arranged along the second direction D2. Each of the bit lines BL may be electrically connected to the first source/drain region SD1. The bit lines BL may include, for example, a metal or a conductive metal nitride. The formation of the bit lines BL may include the formation of the metal-containing layer ML discussed above with reference to FIGS. 5 to 7 according to an example embodiment.

Second capping patterns CP2 may be formed on corresponding bit lines BL. For example, the second capping patterns CP2 may include at least one of SiON, SiCN, SiCON, or SiN.

On the substrate 100, contacts CT may be formed to penetrate the first interlayer dielectric layer 110 and to have connection with corresponding second source/drain regions SD2. Landing pads LP may be formed on corresponding contacts CT. The contacts CT and the landing pads LP may include at least one of a metal or a conductive metal nitride. The formation of the contacts CT and the landing pads LP may include the formation of the metal-containing layer ML discussed above with reference to FIGS. 5 to 7 according to an example embodiment.

Capacitors CAP may be formed on corresponding landing pads LP. The formation of the capacitor CAP may include forming a first electrode LEL1 on the landing pad LP, forming a dielectric layer DIL on the first electrode LEL1, and forming a second electrode LEL2 on the dielectric layer DIL. The first electrode LEL1 may be electrically connected to the second source/drain region SD2 through the landing pad LP and the contact CT.

When viewed in plan as illustrated in FIG. 19, the first electrodes LEL1 may be arranged in a zigzag fashion along the first direction D1. The first electrodes LEL1 may be linearly arranged along the third direction D3.

The first and second electrodes LEL1 and LEL2 may independently include, for example, a metal or a conductive metal nitride. The formation of the first and second electrodes LEL1 and LEL2 may include the formation of the metal-containing layer ML described above with reference to FIGS. 5 to 7 according to an example embodiment.

At least one of the first electrode LEL1 or the second electrode LEL2 may contain the second metal M2 of the co-reactant CRT described above with reference to FIGS. 5 to 7. A content of the second metal M2 contained in at least one of the first electrode LEL1 or the second electrode LEL2 may be, for example, about 0.1 at % to about 10 at %.

Figure 21:
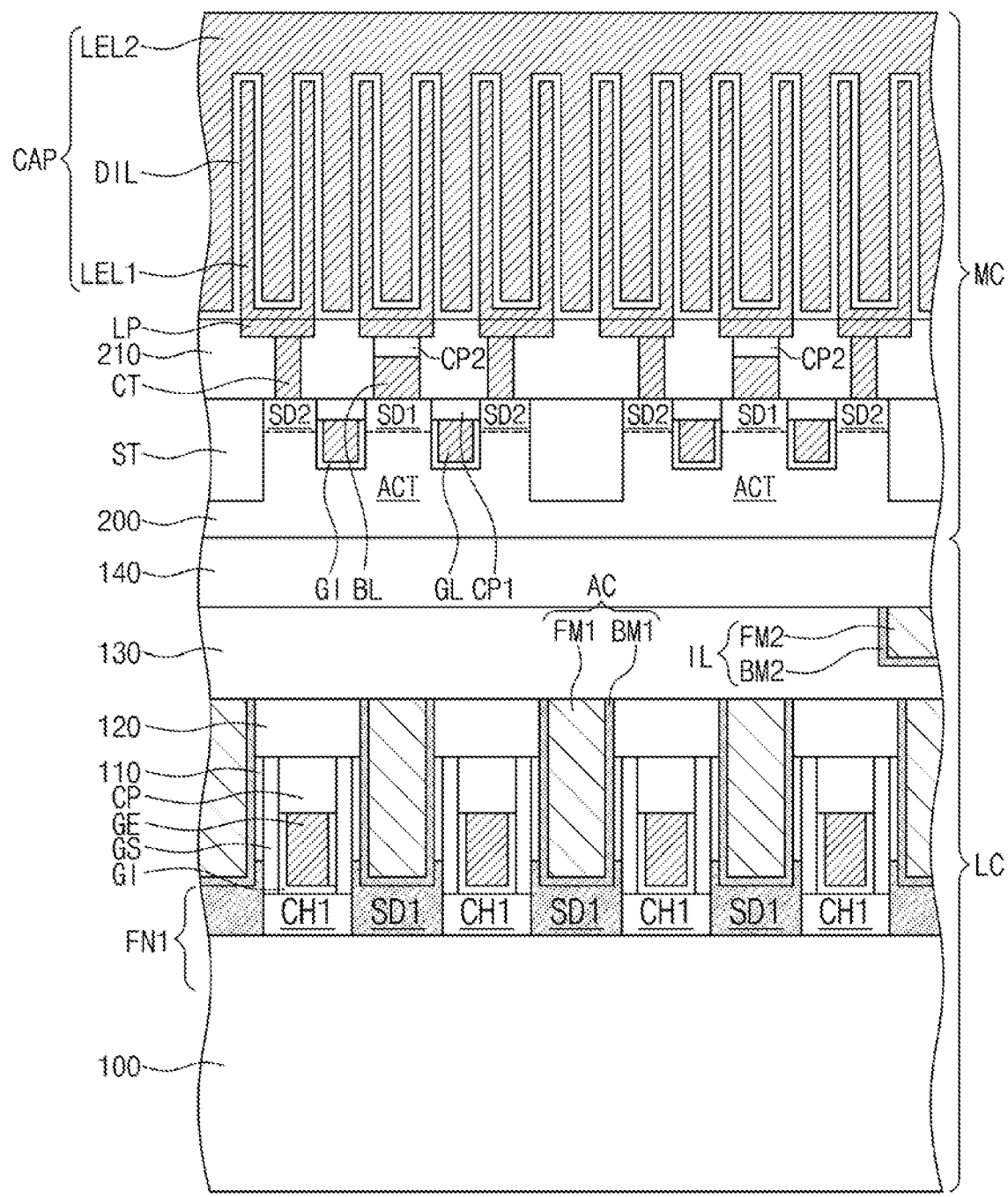
FIG. 21 illustrates a cross-sectional view showing a semiconductor device according to an example embodiment.

FIG. 21 illustrates a cross-sectional view showing a semiconductor device according to an example embodiment. In the description of the example embodiment that follows, a repeated detailed description of elements corresponding with those described above with reference to FIGS. 9 to 20 may be omitted.

Referring to FIG. 21, a logic region LC may be provided that corresponds to a resultant structure of FIGS. 15 and 16A to 16C. The logic region LC may include logic transistors that constitute a logic circuit of a semiconductor device.

A fourth interlayer dielectric layer 140 may be formed on the logic region LC. A memory region MC corresponding to a resultant structure of FIGS. 19 and 20 may be formed on the fourth interlayer dielectric layer 140. The memory region MC may be formed to overlie on the logic region LC. The memory region MC may include a memory cell in which DRAM devices are disposed.

For example, a semiconductor layer 200 of the memory region MC may be formed on the fourth interlayer dielectric layer 140. The semiconductor layer 200 may be substantially the same as the substrate 100 discussed with reference to FIGS. 17 to 20. Memory transistors and capacitors CAP electrically connected thereto may be formed on the semiconductor layer 200. Detailed descriptions about the formation of the memory transistors and the capacitors CAP may be substantially the same as those described above with reference to FIGS. 17 to 20.

While the memory region MC is formed on the logic region LC, the logic transistors in the logic region LC may be exposed to process conditions for the fabrication of the memory region MC. For example, if the memory region MC were to be fabricated at high temperatures (e.g., about 450° C. or higher), the logic transistors of the logic region LC could also be exposed to the high temperatures. In this case, the high temperatures could deteriorate the logic transistors. This situation could have a significant negative influence on reliability of a semiconductor device.

According to an example embodiment, a reducing agent may be used to form a metal-containing layer at low temperatures (e.g., between about 150° C. and 400° C.). For example, when a metal-containing layer is formed to act as the gate line GL, the bit line BL, the contact CT, the landing pad LP, or the capacitor CAP of the memory region MC, a low process temperature may maintain by using the method of forming a metal-containing layer according to an example embodiment. Consequently, it may be possible to prevent deterioration of the logic transistors of the logic region LC and to improve reliability of a semiconductor device.

A method of forming a metal-containing layer according to an example embodiment may use a co-reactant in depositing a metal-containing layer (e.g., a metal nitride layer having conductivity) at low temperatures (e.g., between 150° C. and 400° C.). By forming the metal-containing layer at low temperatures, deterioration of the semiconductor device may be prevented, and reliability may be increased.

As described above, embodiments relate to a method of manufacturing a semiconductor device including a forming method of a metal-containing layer.

By way of summation and review, semiconductor devices have increased integration with the advanced development of the electronic industry. During manufacturing of semiconductor devices, there may be concerns regarding process margin reduction in an exposure process defining fine patterns. Semiconductor devices also have increased in speed with the advanced development of the electronic industry. Various studies have been conducted regarding high integration and/or high speed in semiconductor devices.

A method of forming a metal nitride layer according to an example embodiment may not use plasma and may provide excellent step coverage characteristics. In addition, a safe reactant such as ammonia may be used instead of using a reactant having a strong reactivity. Furthermore, a metal nitride layer formed by a method according to an example embodiment may have a relatively low resistivity, and thus electronic characteristics may be improved.

Embodiments may provide a method of manufacturing a semiconductor device including forming a metal-containing layer using a co-reactant.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A method of manufacturing a semiconductor device, the method comprising:
providing a metal precursor on a substrate; and
providing a reactant and a co-reactant to form a metal nitride layer by reaction with the metal precursor, the reactant being a nitrogen source, the co-reactant being an organometallic compound represented by Chemical Formula 1 below:

[Chemical Formula 1]

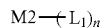

wherein, in Chemical Formula 1, M2 is selected from Sn, In, and Ge, n is 2, 3, or 4, each $L_1$ is independently hydrogen, a halogen, or a functional group represented by Chemical Formula 2 below, provided that at least one $L_1$ is the functional group represented by Chemical Formula 2,

[Chemical Formula 2]

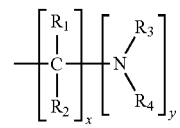

wherein, in Chemical Formula 2, x is 0, 1, 2, 3, 4, or 5 and y is 0 or 1, provided that y is 1 if x is 0, and $R_1$, $R_2$, $R_3$, and $R_4$ are each independently hydrogen, an alkyl group having 1 to 5 carbon atoms, or an aminoalkyl group having 1 to 5 carbon atoms.

2. The method as claimed in claim 1, wherein M2 is Sn.

3. The method as claimed in claim 1, further comprising purging the co-reactant after providing the co-reactant to the metal precursor.

4. The method as claimed in claim 1, wherein the metal precursor includes a metal halide compound or an organometallic compound.

5. The method as claimed in claim 1, wherein the reactant includes one or more of $NH_3$, $N_2H_4$, or Na.

6. The method as claimed in claim 1, wherein the metal nitride layer is formed to have a concentration of M2 that is about 0.1 at % to about 10 at %.

7. The method as claimed in claim 1, wherein forming the metal nitride layer includes performing an atomic layer deposition (ALD) process or a chemical vapor deposition (CVD) process.

8. The method as claimed in claim 1, wherein a process temperature for forming the metal nitride layer is about 150° C. to about 400° C.

9. The method as claimed in claim 1, wherein a process pressure for forming the metal nitride layer is between 0 Torr and about 100 Torr.

10. The method as claimed in claim 1, wherein:
the metal precursor is a titanium precursor, and
the metal nitride layer is formed to have an atomic ratio of nitrogen to titanium that is 0.9 to 1.1.

11. A method of manufacturing a semiconductor device, the method comprising:
forming an active pattern on a substrate;
forming a gate electrode extending across the active pattern;
forming an active contact electrically connected to the active pattern and a gate contact electrically connected to the gate electrode, forming the active contact and the gate contact including forming a first hole exposing the active pattern and a second hole exposing the gate electrode, and forming a first metal nitride layer in the first hole and the second hole,
wherein forming the first metal nitride layer includes:
providing a first metal precursor on the substrate to form a first preliminary layer; and
providing, to the first preliminary layer, a first reactant that is a nitrogen source and a first co-reactant, and
wherein the first co-reactant is an organometallic compound represented by Chemical Formula 1 below:

[Chemical Formula 1]

wherein, in Chemical Formula 1, M2 is selected from Sn, In, and Ge, n is 2, 3, or 4, each $L_1$ is independently hydrogen, a halogen, or a functional group represented by Chemical Formula 2 below, provided that at least one $L_1$ is the functional group represented by Chemical Formula 2,

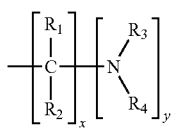

[Chemical Formula 2]

wherein, in Chemical Formula 2, x is 0, 1, 2, 3, 4, or 5 and y is 0 or 1, provided that y is 1 if x is 0, and $R_1$, $R_2$, $R_3$, and $R_4$ are each independently hydrogen, an alkyl group having 1 to 5 carbon atoms, or an aminoalkyl group having 1 to 5 carbon atoms.

12. The method as claimed in claim 11, wherein M2 is Sn.

13. The method as claimed in claim 11, wherein the first reactant includes one or more of $NH_3$, $N_2H_4$, or $N_2$.

14. The method as claimed in claim 11, wherein the first metal nitride layer is formed to have a concentration of M2 that is about 0.1 at % to about 10 at %.

15. The method as claimed in claim 11, further comprising,
forming interconnection lines on the active contact and the gate contact, the interconnection lines being electrically connected to the active contact and the gate contact, and forming the interconnection lines including forming a second metal nitride layer,
wherein forming the second nitride layer includes:
providing a second metal precursor on the substrate to form a second preliminary layer; and
providing, to the second preliminary layer, a second reactant that is a nitrogen source and a second co-reactant, and
wherein the second co-reactant is represented by chemical formula 1 and is a compound that is the same as or different from the first co-reactant.

16. A method of manufacturing a semiconductor device, the method comprising:
forming a first region including a plurality of transistors; and
forming a second region stacked on the first region,
wherein forming the second region includes forming a semiconductor layer on the first region, forming an active pattern on the semiconductor layer, and forming a capacitor electrically connected to the active pattern,
wherein forming the capacitor includes forming a first electrode, forming a dielectric layer on the first electrode, and forming a second electrode on the dielectric layer,
wherein forming at least one of the first and second electrodes includes:
providing a metal precursor to form a preliminary layer, and
providing a reactant that is a nitrogen source and a co-reactant to the preliminary layer, and
wherein the co-reactant is an organometallic compound represented by Chemical Formula 1 below:

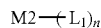

[Chemical Formula 1]

wherein, in Chemical Formula 1, M2 is selected from Sn, In, and Ge, n is 2, 3, or 4, each $L_1$ is independently hydrogen, a halogen, or a functional group represented by Chemical Formula 2 below, provided that at least one $L_1$ is the functional group represented by Chemical Formula 2,

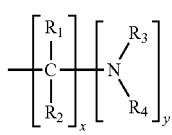

[Chemical Formula 2]

wherein, in Chemical Formula 2, x is 0, 1, 2, 3, 4, or 5 and y is 0 or 1, provided that y is 1 if x is 0, and $R_1$, $R_2$, $R_3$, and $R_4$ are each independently hydrogen, an alkyl group having 1 to 5 carbon atoms, or an aminoalkyl group having 1 to 5 carbon atoms.

17. The method as claimed in claim 16, wherein M2 is Sn.

18. The method as claimed in claim 16, wherein the reactant includes one or more of $NH_3$, $N_2H_4$, or $N_2$.

19. The method as claimed in claim 16, wherein at least one of the first and second electrodes is formed to have a concentration of M2 that is about 0.1 at % to about 10 at %.

20. The method as claimed in claim 16, wherein a process temperature for forming the at least one of the first and second electrodes is about 150° C. to about 400° C.

* * * * *